(12) United States Patent
Igimi et al.

(10) Patent No.: US 8,338,162 B2
(45) Date of Patent: Dec. 25, 2012

(54) OBLIGATELY ANAEROBIC MUTANT LACTIC ACID BACTERIUM AND PREPARATION METHOD THEREFOR, AND EXPRESSION VECTOR FUNCTIONING IN OBLIGATELY ANAEROBIC LACTIC ACID BACTERIUM

(75) Inventors: Shizunobu Igimi, Tokyo (JP); Minoru Fujimori, Ibaraki (JP); Shun'ichiro Taniguchi, Nagano (JP); Michihiko Harada, Nagano (JP); Takayuki Sasaki, Nagano (JP); Akinobu Kajikawa, Yokohama (JP)

(73) Assignee: Anaeropharma Science, Inc., Tokyo (JP)

( * ) Notice: Subject to any disclaimer, the term of this patent is extended or adjusted under 35 U.S.C. 154(b) by 713 days.

(21) Appl. No.: 12/426,152

(22) Filed: Apr. 17, 2009

(65) Prior Publication Data

US 2010/0266545 A1 Oct. 21, 2010

(51) Int. Cl.
*C12N 1/21* (2006.01)
*C12N 15/74* (2006.01)
*C12N 15/00* (2006.01)

(52) U.S. Cl. ............ 435/252.3; 435/252.9; 435/471; 435/320.1

(58) Field of Classification Search .................. None
See application file for complete search history.

(56) References Cited

U.S. PATENT DOCUMENTS

| | | | |
|---|---|---|---|
| 2008/0193577 | A1 | 8/2008 | Yamashita et al. |
| 2009/0169516 | A1 | 7/2009 | Shimatani et al. |
| 2009/0264513 | A1* | 10/2009 | Shimatani-Shibata et al. . 514/44 R |
| 2009/0280091 | A1 | 11/2009 | Hamaji et al. |

FOREIGN PATENT DOCUMENTS

| | | |
|---|---|---|
| EP | 1 867 714 A1 | 12/2007 |
| EP | 1 978 099 A1 | 10/2008 |
| EP | 2 019 138 A1 | 1/2009 |
| JP | 04-235920 | 8/1992 |
| JP | 06-080575 | 3/1994 |
| JP | 07-228536 | 8/1995 |
| JP | 09-002959 | 1/1997 |
| JP | 09-030981 | 2/1997 |
| JP | 09-249574 | 9/1997 |
| JP | 09-301878 | 11/1997 |
| JP | 10-029946 | 2/1998 |
| JP | 10-139674 | 5/1998 |
| JP | 11-199494 | 7/1999 |
| JP | 2002-097144 | 4/2002 |
| WO | WO 2006/109619 A1 | 10/2006 |
| WO | WO 2007/052356 | 5/2007 |
| WO | WO 2007/136107 A1 | 11/2007 |

OTHER PUBLICATIONS

Yazawa, et al., "*Bifidobacterium longum* as a delivery system for cancer gene therapy: Selective localization and growth in hypoxic tumors," Cancer Gene Therapy, vol. 7, No. 2, 2000, pp. 269-274.

Yazawa, et al., *Bifidobacterium longum* as a delivery system for gene therapy of chemically induced rat mammary tumors, Breast Cancer Res. and Treat., 66, 2001, pp. 165-170.

Nakamura, et al., "Cloned cytosine deaminase gene expression of *Bifidobacterium longum* and application to enzyme/pro-drug therapy of hypoxic solid tumors," Biosci. Biotechnol. Biochem., 66 (11), 2002, pp. 2362-2366.

Fujimori, et al., "The genus *Bifidobacterium* for cancer gene therapy," Current Opin. In Drug Discov. and Develop., vol. 5, No. 2, 2002, pp. 200-203.

Fujimori, "Anaerobic bacteria as a gene delivery system for breast cancer therapy", 2008, vol. 66, No. 6, pp. 1211-1218.

Igimi, "S-1: Development of new functions of lactic acid bacteria by genetic recombination technology", Microbiol Culture Collections, Jun. 2008, vol. 24, No. 1. p. 43.

Matsumura, et al., "Construction of secretion-expression vector for lactic acid bacteria (4th report)", abstract of papers, the 24th Annual Meeting of the Pharma Society of Japan Kyushu Branch, Nov. 2007, p. 175.

* cited by examiner

*Primary Examiner* — Maria Marvich
(74) *Attorney, Agent, or Firm* — Jones Day

(57) ABSTRACT

The present invention provides an obligately anaerobic lactic acid bacterium having no risk of causing side effects in normal tissue and promising as a safe therapeutic agent and a gene transporter for a disease that is in an anaerobic environment such as a solid tumor, a preparation method therefor, and an expression vector useful in the preparation method. The obligately anaerobic lactic acid bacterium of the present invention has been artificially mutated from being facultatively anaerobic to being obligately anaerobic and, furthermore, is capable of being transformed by an expression vector having introduced thereinto a gene for expressing an active protein useful for the treatment of a disease that is in an anaerobic environment. Furthermore, the expression vector of the present invention functions in an obligately anaerobic lactic acid bacterium and contains a *Lactobacillus*-derived plasmid replication protein gene (Rep), a secretion signal sequence (PslpA-SSartP) comprising a *Lactobacillus*-derived s-layer gene promoter and a *Lactobacillus*-derived PrtP protein secretion signal, and one or more selection marker genes. The expression vector of the present invention enables producing an extremely safe and excellent therapeutic agent and gene transporting microorganism for a disease that is in an anaerobic environment.

12 Claims, 6 Drawing Sheets

*in vitro* CULTURING OF Lactobacillus casei KJ686

UNDER AEROBIC CONDITIONS AT 37°C

UNDER ANAEROBIC CONDITIONS AT 37°C

SEQUENCE LISTING

<160> NUMBER OF SEQ ID NOS: 6

<210> SEQ ID NO 1
<211> LENGTH: 7657
<212> TYPE: DNA
<213> ORGANISM: Artificial sequence
<220> FEATURE:
<223> OTHER INFORMATION: pLPD8s hIL-2

<400> SEQUENCE: 1

```
tatagtgtca cctaaatcgt atgtgtatga tacataaggt tatgtattaa ttgtagccgc     60
gttctaacga caatatgtac aagcctaatt gtgtagcatc tggcttactg aagcagaccc    120
tatcatctct ctcgtaaact gccgtcagag tcggtttggt tggacgaacc ttctgagttt    180
ctggtaacgc cgttccgcac cccggaaatg gtcagcgaac caatcagcag ggtcatcgct    240
agccagatcc tctacgccgg acgcatcgtg gccggcatca ccggcgccac aggtgcggtt    300
gctggcgcct atatcgccga catcaccgat ggggaagatc gggctcgcca cttcgggctc    360
atgagcgctt gtttcggcgt gggtatggtg gcaggccccg tggccggggg actgttgggc    420
gccatctcct tgcaccattc cttgcggcgg cggtgctcaa cggcctcaac ctactactgg    480
gctgcttcct aatgcaggag tcgcataagg gagagcgtcg atatggtgca ctctcagtac    540
aatctgctct gatgccgcat agttaagcca gccccgacac ccgccaacac ccgctgacgc    600
gccctgacgg gcttgtctgc tcccggcatc cgcttacaga caagctgtga ccgtctccgg    660
gagctgcatg tgtcagaggt tttcaccgtc atcaccgaaa cgcgcgagac gaaagggcct    720
cgtgatacgc ctattttat aggttaatgt catgataata atggtttctt agacgtcagg    780
tggcactttt cggggaaatg tgcgcggaac ccctatttgt ttattttct aaatacattc    840 aaatatgtat ccgctcatga dacaataacc ctgataaatg cttcaataat attgaaaaag    900
gaagagtatg agtattcaac atttccgtgt cgcccttatt ccctttttg cggcattttg    960 ccttcctgtt tttgctcacc cagaaacgct ggtgaaagta aaagatgctg aagatcagtt   1020
gggtgcacga gtgggttaca tcgaactgga tctcaacagc ggtaagatcc ttgagagttt   1080
tcgccccgaa gaacgttttc caatgatgag cacttttaaa gttctgctat gtggcgcggt   1140
attatcccgt attgacgccg ggcaagagca actcggtcgc cgcatacact attctcagaa   1200
tgacttggtt gagtactcac cagtcacaga aaagcatctt acggatggca tgacagtaag   1260
agaattatgc agtgctgcca taaccatgag tgataacact gcggccaact tacttctgac   1320
aacgatcgga ggaccgaagg agctaaccgc ttttttgcac aacatggggg atcatgtaac   1380
tcgccttgat cgttgggaac cggagctgaa tgaagccata ccaaacgacg agcgtgacac   1440
cacgatgcct gtagcaatgg caacaacgtt gcgcaaacta ttaactggcg aactacttac   1500
tctagcttcc cggcaacaat taatagactg gatgaggcg gataaagttg caggaccact   1560
tctgcgctcg gcccttccgg ctggctggtt tattgctgat aaatctggag ccggtgagcg   1620
tgggtctcgc ggtatcattg cagcactggg gccagatggt aagccctccc gtatcgtagt   1680
tatctacacg acggggagtc aggcaactat ggatgaacga aatagacaga tcgctgagat   1740
aggtgcctca ctgattaagc attggtaact gtcagaccaa gtttactcat atatacttta   1800
```

-continued

```
gattgattta aaacttcatt tttaatttaa aaggatctag gtgaagatcc ttttttgataa    1860 tctcatgacc aaaatcccett aacgtgagtt ttcgttccac tgagcgtcag accccgtaga    1920
aaagatcaaa ggatcttctt gagatccttt ttttctgcgc gtaatctgct gcttgcaaac    1980
aaaaaaacca ccgctaccag cggtggtttg tttgccggat caagagctac caactctttt    2040
tccgaaggta actggcttca gcagagcgca gataccaaat actgtccttc tagtgtagcc    2100
gtagttaggc caccacttca agaactctgt agcaccgcct acatacctcg ctctgctaat    2160
cctgttacca gtggctgctg ccagtggcga taagtcgtgt cttaccgggt tggactcaag    2220
acgatagtta ccggataagg cgcagcggtc gggctgaacg ggggggttcgt gcacacagcc    2280 cagcttggag cgaacgacct acaccgaact gagatacccta cagcgtgagc tatgagaaag    2340
cgccacgctt cccgaaggga aaaggcgga caggtatccg gtaagcggca gggtcggaac    2400
aggagagcgc acgagggagc ttccaggggg aaacgcctgg tatctttata gtcctgtcgg    2460
gtttcgccac ctctgacttg agcgtcgatt tttgtgatgc tcgtcagggg ggcggagcct    2520
atggaaaaac gccagcaacg cggccttttt acggttcctg gccttttgct ggccttttgc    2580
tcacatgttc tttcctgcgt tatcccctga ttctgtggat aaccgtatta ccgcctttga    2640
gtgagctgat accgctcgcc gcagccgaac gaccgagcgc agcgagtcag tgagcgagga    2700
agcggaagag cgcccaatac gcaaaccgcc tctccccgcg cgttggccga ttcattaatg    2760
cagctggctt atcgaaatta atacgactca ctatagggag accggaattc gctccgctca    2820
aactaaaact gacaagtcag tttgaaccce aaaaagcaga taagttcagt cgtaaactcc    2880
ttccgaactt ttctccctttt tgagttgctc tcagaagccc aaaattgcct tctaagccat    2940
tttaagaatt aacaagttat ttaactgtct gtcaacggta aatcgacgta gatagccttta    3000 ttgagccgta caggcgaaat tagactatct aggaggcttt aaggagttga tagactttgc    3060
aaattaaaag ctaaaggcg gaaagcagct tgcctgtttt cccgagcccg actggcggcg    3120
aagtcgaaac ggtcaagctg gttcagcttg tcaggtttgg gtgaaaccca aggtcttact    3180
ttttcggtcg ttaaaactgg aaaatttcat aaaattttg gtgggtctct ctaactagcc    3240
cgctacccgt tcgaaaatcg aaccttttgc ttttttattgt gaacaaaaat gtggtaatgt    3300
tctagagttt tagaaagaga tttaaggggg attaataatg ccgagaattg acgaacgtag    3360
ttggaaaaag atttttgaat tgagtaataa cggtaaatac gatgatgaag cgtatgctga    3420
gattcttgct acagtattga atttgcgtat tgaatttggc gtgttgaaaa aggcttaact    3480
caaagtgacg ttgcgagaat atctggttta tctacgatgt atgatctcta aaattgagag    3540
tcaatataca gtaccgagtg taaaaaattt cttacgatat attttcgcct tagatttgga    3600
ttgggaactt gttcataaat gttaactgaa ttttgggttt aaaaaagagg ttcagtatga    3660
acctcttttt tggggttttg aaagtgacgt ttttgtcact ttcctcttat cttgatacag    3720
tagaatcaat tcgttttttt gtttttcatt taaagccttg acatggcggg gtttaggcgt    3780
aaaattagcc tcataaatgg tgaattgaaa acaaaataaa aaacccacgt gaaatctctg    3840
tttggcgacc gagcacgtga gttgattatc atttgcgatt tatagcctta ttctagggg     3900 taaaccctat gatgtcaagg ctgtaaactt agctaaaatg ataattcagc ccttcacgt    3960 ggataaaacg ggaggagctt tttatgtctg aagtgtttaa agacgttaca acaaatggaa    4020
aagtaagacc ttggcgagac cgcaaaattg aaaatgtacg ctatgcagaa tatttgtcga    4080
ttttagaatt taagcgggcg catgatgtcc gaggctgtgg tgaaaatttta cgttttcgga    4140 agattgggga gcatttaaaa ctgtatcaga cttggttttg caaaaagcgg ttgtgtccgt    4200
```

```
tatgcaattg gagaaagagt atgaaaaatt cgagccaatt aaaacaaatt attgcagagg    4260
cagttgtgag agagcctaaa ggacggtttt tgtttttaac tttgaccgtt aagaatgctt    4320
attcagcaga agagttaaaa tcctcgttga gagctttgac taaggctttt ggcaagttat    4380
cgcgttataa aaaagtatca aagaacttac taggttactt acgctcaacg gaaattacag    4440
tgaacgaaca tgacggctca tataatcaac atttgcatgt cttgctgttt gtaaggtcta    4500
gctatttcaa gtcgagtgac agttatatta atcaagaaga atggacaaga ctgtggcaaa    4560
aggcgttaaa agtcgattat gagccagtgg tgcatgtgca agtcgttaag gcaaataaac    4620
gaaaagggac ggattcttta caagctagtg cggaagaaac ggctaagtat gaagtaaaat    4680
cggctgatta tatgacggtt gatgatgagc gtaatttggt ggtgattaaa aatttggagt    4740
atgccttagc tggaacacga caaatcagct atggtggtct gtttaagcaa attaagcaag    4800
acttgaaact ggaagatgtt gaaaatggtg atttaattca tgttggcgat gaagattaca    4860
ccaaagagca aatggaagct gcggaagaag tcgttgcaaa gtgggacttt aaaaagcaaa    4920 attatttat ttggtaaaga gaatgtaggg tatgatcaac ggcaaaaccg ttgggccata    4980
cccttatttt ttgttgccag cttgctgact tctgatacag ttttttttggt tttagcacta    5040 ctccaattta tttggagtgt aagtgcgcct tgaactaatg ttttgaattt tgtcattgtc    5100
gaaatataag acaatggcgc acttacacgt cactttcatg acgattcaca aaaaataggc    5160
acacgaaaaa caagttaagg gatgcagttt atgcatccct taacttactt attaaataat    5220
ttatagctat tgaaaagaga taagaattgt tcaaagctaa tattgtttaa atcgtcaatt    5280
cctgcatgtt ttaaggaatt gttaaattga ttttttgtaa atattttctt gtattctttg    5340
ttaacccatt tcataacgaa ataattatac ttttgtttat ctttgtgtga tattcttgat    5400 tttttttctac ttaatctgat aagtgagcta ttcactttag gtttaggatg aaaatattct    5460
cttgaaacca tacttaatat agaaaatatca acttctgcca ttaaaagtaa tgccaatgag    5520
cgttttgtat ttaataatct tttagcaaac ccgtattcca cgattaaata aatctcatta    5580
gctatactat caaaaacaat tttgcgtatt atatccgtac ttatgttata aggtatatta    5640
ccatatattt tataggattg ttttttagga aatttaaact gcaatatatc cttgtttaaa    5700
acttggaaat tatcgtgatc aacaagttta ttttctgtag ttttgcataa tttatggtct    5760
atttcaatgg cagttacgaa attacacctc tttactaatt caagggtaaa atggccttt    5820 cctgagccga tttcaaagat attatcatgt tcatttaatc ttatatttgt cattatttta    5880
tctatattat gttttgaagt aataaagttt tgactgtgtt ttatattttt ctcgttcatt    5940
ataaccctct ttaatttggt tatatgaatt ttgcttatta acgattcatt ataaccactt    6000
attttttgtt tggttgataa tgaactgtgc tgattacaaa aatactaaaa atgcccatat    6060
tttttcctcc ttataaaatt agtataatta tagcacgagc tctgataaat atgaacatga    6120
tgagtgatcg ttaaatttat actgcaatcg gatgcgatta ttgaataaaa gatatgagag    6180
atttatctaa tttctttttt cttgtaaaaa aagaaagttc ttaaaggttt tatagttttg    6240
gtcgtagagc acacggttta acgacttaat tacgaagtaa ataagtctag tgtgttagac    6300
tttatgaaat ctatatacgt ttatatatat ttattatccg tcgtgcgttc tgactgcaaa    6360
acgtcagaag ggcgcacttg caccccacca aataaatggg gtgcaagttg cttaaaacct    6420
gtctcagaat tcagatctga ttacaaaggc tttaagcagg ttagtgacgt tttagttatg    6480
taacaataac attacaggac acccataatt gtttcaatcc aacgacaatc agagcgtaat    6540
ccttgtatct ccttaaggaa atcgctatac ttatcttcgt agttagggga tagctgatcg    6600
```

```
ggtccgctaa tgttatgaaa taaaattctt aacaaaagcg gccgcttcgg ttatactatt    6660
cttgcttgat aaattacata ttttatgttt gtggagggta ttggatgcaa aggaaaagaa    6720
aagggctatc gatcttgtta gccggtacag tcgctttagg ggcgctggct gtcttgccag    6780
tcggcgaaat ccaagcaaag gcggctatct cgcagcaaac taaggtatca tcactcgcaa    6840
atacggttaa ggccgcgact gctaagcaag cggccactga cacaaccgca gcgacaacga    6900
atcaagcgat tgccacacag ttggcggcta aaggtattga ttacaaggat ccgagtgcac    6960
ctacttcaag ttctcaaaag aaaacacagc tacaactgga gcatttactg ctggatttac    7020
agatgatttt gaatggaatt aataattaca agaatcccaa actcaccagg atgctcacat    7080
ttaagtttta catgcccaag aaggccacag aactgaaaca tcttcagtgt ctagaagaag    7140
aactcaaacc tctggaggaa gtgctaaatt tagctcaaag caaaaacttt cacttaagac    7200
ccagggactt aatcagcaat atcaacgtaa tagttctgga actaaaggga tctgaaacaa    7260
cattcatgtg tgaatatgct gatgagacag caaccattgt agaatttctg aacagatgga    7320
ttaccttttg tcaaagcatc atctcaacac tgacttgact cgagtaatgt aaggtcaccc    7380
tagagtcaac taaaagccac tactgtaata gttaaaattg tttaaaagag gaaatcagtt    7440
tgttatcagt tgatttcctc ttttatgtat cactgttttc agagtaagtt ccaatggctg    7500
gcattgctgt taatatgaca ctagatgata taagttatca tgttaagctc gatggtaagt    7560
tgggtttaat tgatagaaaa cataatagtt atgagatgct tgaaatacct actaaaaata    7620 cattttacc aaattttata tgatccggcc ggtattc                              7657

<210> SEQ ID NO 2
<211> LENGTH: 951
<212> TYPE: DNA
<213> ORGANISM: Lactobacillus casei

<400> SEQUENCE: 2
tgtctgaagt gtttaaagac gttacaacaa atggaaaagt aagaccttgg cgagaccgca      60
aaattgaaaa tgtacgctat gcagaatatt tgtcgatttt agaatttaag cgggcgcatg     120
atgtccgagg ctgtggtgaa attttacgtt ttcggaagat tggggagcat ttaaaactgt     180
atcagacttg gttttgcaaa aagcggttgt gtccgttatg caattggaga aagagtatga     240
aaaattcgag ccaattaaaa caaattattg cagaggcagt tgtgagagag cctaaaggac     300
ggtttttgtt tttaactttg accgttaaga atgcttattc agcagaagag ttaaaatcct     360
cgttgagagc tttgactaag gcttttggca agttatcgcg ttataaaaaa gtatcaaaga     420
acttactagg ttacttacgc tcaacggaaa ttacagtgaa cgaacatgac ggctcatata     480
atcaacattt gcatgtcttg ctgtttgtaa ggtctagcta tttcaagtcg agtgacagtt     540
atattaatca agaagaatgg acaagactgt ggcaaaaggc gttaaaagtc gattatgagc     600
cagtggtgca tgtgcaagtc gttaaggcaa ataaacgaaa agggacggat tctttacaag     660
ctagtgcgga agaaacggct aagtatgaag taaaatcggc tgattatatg acggttgatg     720
atgagcgtaa tttggtggtg attaaaaatt tggagtatgc cttagctgga acacgacaaa     780
tcagctatgg tggtctgttt aagcaaatta agcaagactt gaaactggaa gatgttgaaa     840
atggtgattt aattcatgtt ggcgatgaag attacaccaa agagcaaatg gaagctgcgg     900
aagaagtcgt tgcaaagtgg gactttaaaa agcaaaatta ttttatttgg t              951
```

```
<210> SEQ ID NO 3
<211> LENGTH: 508
<212> TYPE: DNA
<213> ORGANISM: Artificial sequence
<220> FEATURE:
<223> OTHER INFORMATION: PslpA-SSprtP fusion

<400> SEQUENCE: 3
attacaaagg ctttaagcag gttagtgacg ttttagttat gtaacaataa cattacagga       60
cacccataat tgtttcaatc caacgacaat cagagcgtaa tccttgtatc tccttaagga      120
aatcgctata cttatcttcg tagttagggg atagctgatc gggtccgcta atgttatgaa      180
ataaaattct taacaaaagc ggccgcttcg gttatactat tcttgcttga taaattacat      240
attttatgtt tgtggagggt attggatgca aaggaaaaag aaagggctat cgatcttgtt      300
agccggtaca gtcgctttag gggcgctggc tgtcttgcca gtcggcgaaa tccaagcaaa      360
ggcggctatc tcgcagcaaa ctaaggtatc atcactcgca aatacggtta aggccgcgac      420
tgctaagcaa gcggccactg acacaaccgc agcgacaacg aatcaagcga ttgccacaca      480
gttggcggct aaaggtattg attacaag                                          508

<210> SEQ ID NO 4
<211> LENGTH: 405
<212> TYPE: DNA
<213> ORGANISM: Homo sapiens

<400> SEQUENCE: 4
gtgcacctac ttcaagttct acaaagaaaa cacagctaca actggagcat ttactgctgg       60
atttacagat gattttgaat ggaattaata attacaagaa tcccaaactc accaggatgc      120
tcacatttaa gttttacatg cccaagaagg ccacagaact gaaacatctt cagtgtctag      180
aagaagaact caaacctctg gaggaagtgc taaatttagc tcaaagcaaa aactttcact      240
taagacccag ggacttaatc agcaaatatca acgtaatagt tctggaacta aagggatctg      300
aaacaacatt catgtgtgaa tatgctgatg agacagcaac cattgtagaa tttctgaaca      360
gatggattac cttttgtcaa agcatcatct caacactgac ttgac                       405

<210> SEQ ID NO 5
<211> LENGTH: 31
<212> TYPE: DNA
<213> ORGANISM: Artificial sequence
<220> FEATURE:
<223> OTHER INFORMATION: human IL-2 primer F

<400> SEQUENCE: 5
ccccggatcc gagtgcacct acttcaagtt c                                       31

<210> SEQ ID NO 6
<211> LENGTH: 30
<212> TYPE: DNA
<213> ORGANISM: Artificial sequence
<220> FEATURE:
<223> OTHER INFORMATION: human IL-2 primer R

<400> SEQUENCE: 6
ccccctcgag tcaagttagt gttgagatga                                         30
```

OBLIGATELY ANAEROBIC MUTANT LACTIC ACID BACTERIUM AND PREPARATION METHOD THEREFOR, AND EXPRESSION VECTOR FUNCTIONING IN OBLIGATELY ANAEROBIC LACTIC ACID BACTERIUM

FIELD OF THE INVENTION

The present invention relates to a lactic acid bacterium, useful as a therapeutic agent for a disease that is in an anaerobic environment such as a solid tumor, the lactic acid bacterium has been mutated from being facultatively anaerobic to being obligately anaerobic, a preparation method therefor, and an expression vector functioning in an obligately anaerobic lactic acid bacterium. More particularly, the present invention relates to an obligately anaerobic lactic acid bacterium that has been mutated from being facultatively anaerobic to being obligately anaerobic so that the bacterium does not grow or has a very low growth rate in an aerobic environment, but is capable of growing in an anaerobic environment. The present invention further relates to an obligately anaerobic lactic acid bacterium that is capable of being transformed with an expression vector, a preparation method therefor, a pharmaceutical composition comprising the obligately anaerobic lactic acid bacterium as an active ingredient, and an expression vector that is capable of functioning in an obligately anaerobic lactic acid bacterium and promoting good protein expression and protein secretion.

BACKGROUND

'Lactic acid bacterium' is a general term for bacteria that decompose sugar to produce lactic acid, thus generating energy, and includes *Lactobacillus* genus bacteria, *Bifidobacterium* genus bacteria, *Lactococcus* genus bacteria, *Streptococcus* genus bacteria, and *Enterococcus* genus bacteria.

Bacteria can be roughly divided, in terms of oxygen demand for their growth, into aerobes, which require oxygen for growth, and anaerobes, which do not require oxygen. Furthermore, the anaerobes can be divided into obligatory anaerobes, which cannot grow in the presence of oxygen, and facultative anaerobes, which can grow in either the presence or absence of oxygen.

Among the lactic acid bacteria above, *Bifidobacterium* genus bacteria are obligatory anaerobes, and *Lactobacillus* genus bacteria, *Lactococcus* genus bacteria, *Streptococcus* genus bacteria, *Enterococcus* genus bacteria, etc. are facultative anaerobes.

Lactic acid bacteria are conventionally commonly used in the food field, and recently their effect as probiotics of promote health maintenance of a host by improving the balance of enterobacterial flora has been noted.

Furthermore, there have been a number of reports relating to their applications in the medicinal field, and with regard to the treatment of a tumor, in addition to direct application as an antitumor drug, applications as an immunostimulant, an IgE production inhibitor, a humoral immunity recovery agent, an interleukin 12 production promoter, etc. have been reported.

For example, it has been reported that a composition comprising one or more selected from *Lactobacillus* genus bacteria, *Bifidobacterium* genus bacteria, *Pediococcus* genus bacteria, *Streptococcus* genus bacteria, and *Leuconostoc* genus bacteria exhibits an immunostimulatory action (antitumor activity) (ref. e.g. Patent Publication 1).

In addition, various types of useful lactic acid bacteria have been reported as a therapeutic agents for tumor such as an antitumor drug, an IgE production inhibitor, a humoral immunity recovery agent, an interleukin 12 production promoter, an immunostimulant (ref. e.g. Patent Publications 2 to 7).

Furthermore, with regard to *Lactobacillus* genus bacteria in particular, there have been reported *Lactobacillus* genus bacteria that are useful as tumor growth inhibitors or malignant tumor recurrence inhibitors (ref. e.g. Patent Publications 8 to 11).

However, as described above, among these lactic acid bacteria, all other than the *Bifidobacterium* genus bacteria are facultative anaerobes, which grow in an environment having a relatively high oxygen concentration. Therefore, naturally these bacteria is highly likely to accumulate and grow in normal tissue as well as in tumor tissue that is in an anaerobic environment, and the occurrence of side effects in the normal tissue is concerned.

On the other hand, with regard to *Bifidobacterium* genus bacteria, which are obligatory anaerobes, methods for using them in the treatment of a disease that is in an anaerobic environment such as a solid tumor have been proposed.

For example, *Bifidobacterium longum*, which is a *Bifidobacterium* genus bacterium, has been confirmed that, upon systemic intravenous administration, it quickly disappears from normal tissue and specifically accumulates and grows in the solid tumor region, and its application to the treatment of a solid tumor is anticipated (ref. e.g. Non-patent Publications 1 and 2).

Further, *Bifidobacterium longum* was transformed to express cytosine deaminase (hereinafter, called CD) as a target active protein, which is an enzyme that converts 5-fluorocytosine (hereinafter, called 5-FC), which is a prodrug (precursor) of 5-fluorouracil (hereinafter, called 5-FU) with antitumor activity, into 5-FU, and has been confirmed that, upon being intravenously administrated, the bacteria specifically accumulate and grow in the tumor site and express the target protein, and it has been reported that the bacterium is very promising as a safe therapeutic agent for solid tumor having no possibility of inducing side effects in normal tissue (ref. e.g. Patent Publication 12 and Non-patent Publications 3 and 4).

PRIOR ART PUBLICATIONS

[Patent Publication 1] JP, A, 6-80575
[Patent Publication 2] JP, A, 2002-97144
[Patent Publication 3] JP, A, 9-2959
[Patent Publication 4] JP, A, 9-249574
[Patent Publication 5] JP, A, 10-29946
[Patent Publication 6] JP, A, 10-139674
[Patent Publication 7] JP, A, 11-199494
[Patent Publication 8] JP, A, 7-228536
[Patent Publication 9] JP, A, 9-30981
[Patent Publication 10] JP, A, 9-301878
[Patent Publication 11] Japanese Patent No. 3014148
[Non-patent Publication 1] Yazawa et al., Cancer Gene Ther., 7, 269-274 (2000)
[Non-patent Publication 2] Yazawa et al., Brepast Cancer Reps. Trepat., 66, 165-170 (2001)
[Non-patent Publication 3] Nakamura et al., Biosci. Biotechnol. Biochem., 66, 2362-2366 (2002)
[Non-patent Publication 4] Fujimori et al., Curr. Opin. Drug Discov. Devel., 5, 200-203 (2002)

SUMMARY OF INVENTION

Problems to be Solved by the Invention

Lactic acid bacteria such as *Lactobacillus* genus bacteria, *Bifidobacterium* genus bacteria, *Pediococcus* genus bacteria, *Streptococcus* genus bacteria, and *Leuconostoc* genus bacteria are already known to have useful effects as tumor therapeutic agents such as antitumor drugs, IgE production inhibitors, humoral immunity recovery agents, interleukin 12 production promoters, and immunostimulants.

When a microorganism is used as a disease therapeutic agent for a disease such as a malignant tumor that is in an anaerobic environment such as a malignant tumor, in order to exhibit an antitumor effect only in tumor tissue that is in an anaerobic environment and not exhibit the effect in normal tissue that is not in an anaerobic environment, the microorganism is desirably an obligatory anaerobe that specifically accumulates or colonizes and proliferates in the tumor tissue that is in an anaerobic environment and does not colonize or proliferate in normal tissue that is not in an anaerobic environment.

However, among the lactic acid bacteria above, none of the lactic acid bacteria other than *Bifidobacterium* genus bacteria are obligatory anaerobes but are facultative anaerobes, which can grow even in an aerobic environment.

Therefore, when the facultatively anaerobic lactic acid bacteria, other than the *Bifidobacterium* genus bacteria, are systemically administered by intravenous injection, the bacteria colonize and proliferate not only in the tumor tissue that is in an anaerobic environment but also in normal tissue, and highly likely to induce side effects on the normal tissue.

Because of this, lactic acid bacteria other than *Bifidobacterium* genus bacteria are limited to be administrated orally, intratumorally or intramuscularly when used as an antitumor drug, the method of application is restricted. Furthermore, even in the case of oral administration or intratumoral administration, there is a possibility of viable cells penetrating into a blood vessel from the intestinal tract or spreading out of the tumor tissue, resulting the colonization and proliferation in normal tissue, inducing side effects on the normal tissue.

Therefore, in the field of antitumor treatment, there has been a desire for the development of lactic acid bacteria, other than *Bifidobacterium*, that have been mutated from being facultatively anaerobic to being obligately anaerobic.

On the other hand, it is known that, among lactic acid bacteria other than *Bifidobacterium*, for example, in *Lactobacillus* genus bacteria, due to spontaneous mutation, evolution, etc. there is an obligatory anaerobe having very low growth ability in an aerobic environment (hereinafter, called a natural mutant type obligatory anaerobe). For example, *Lactobacillus johnsonii* JCM 2012$^T$ strain, *Lactobacillus ruminis*, etc. are known.

A transgenic vector of a lactic acid bacterium generally has high host specificity, and examination at the strain level is necessary. An expression vector generally used for gene recombination of a lactic acid bacterium, such as pLP401, pLP402, or pLP403 (hereinafter, called a pLP400 series vector) cannot function in natural mutant type obligatory anaerobes such as the previously reported *Lactobacillus johnsonii* JCM 2012$^T$ strain and *Lactobacillus ruminis* described above, and in order to transform them so as to express an active protein having antitumor activity, it is necessary to newly develop an expression vector for the strain. Therefore, these natural mutant type obligatory anaerobes cannot be used as parent bacteria for a gene transporter useful as a therapeutic agent for a disease that is in an anaerobic environment.

Furthermore, an expression vector such as a lactic acid bacterium—*Escherichia coli* (*E. coli*) shuttle vector into which a gene has been introduced for expressing a protein having activity of converting an antitumor substance precursor into an antitumor substance, and a lactic acid bacterium of the *Bifidobacterium* genus transformed using the expression vector, have already been known.

However, conventional expression vectors have a disadvantage that expression of a recombinant protein by the introduced active protein-expressing gene is suppressed in a medium containing glucose as a sugar source.

Moreover, a lactic acid bacterium of the *Bifidobacterium* genus transformed using a conventional expression vector does not extracellularly secrete the active protein produced within the bacterial cell, the effect of a recombinant protein from the introduced active protein-expressing gene was not able be fully exhibited depending on the purpose of the treatment and the case of a disease that is in an anaerobic environment.

Therefore, in the antitumor treatment field, there has been a desire for the development of an expression vector that can function in an anaerobe and can introduce a bacterium a gene for expressing a protein having activity useful for the treatment of a disease that is in an anaerobic environment and transform the bacterium to efficiently produce and extracellularly secrete the active protein.

It is therefore an object of the present invention to solve the above-mentioned problems and thus provide a lactic acid bacterium that has been mutated from being facultatively anaerobic to being obligately anaerobic so that it does not grow or has a very low growth rate in an aerobic environment but grows in an anaerobic environment, an obligately anaerobic mutant lactic acid bacterium that can be transformed by an expression vector such as an anaerobe-derived plasmid into which has been introduced a gene for expressing a protein having activity useful for the treatment of a disease that is in an anaerobic environment and a preparation method for the obligately anaerobic mutant lactic acid bacterium, and a pharmaceutical composition containing the obligately anaerobic lactic acid bacterium as an active ingredient.

It is another object of the present invention to solve the above-mentioned problems and thus provide an expression vector that can function in an obligately anaerobic lactic acid bacterium and can introduce the bacterium a gene for expressing a protein having activity useful for the treatment of a disease that is in an anaerobic environment and transform the bacterium to be capable of producing and extracellularly secreting the active protein.

Means for Solving the Problems

As a result of an intensive investigation by the present inventors in order to solve the above-mentioned problems, it has been found that chemically mutating a wild-type lactic acid bacterium enables a mutation from a facultative anaerobe to an obligatory anaerobe. Furthermore, it has been found that introducing a marker gene into the mutant lactic acid bacterium, and, by using the marker as an index, selecting bacteria capable of being transformed enables obtaining an obligately anaerobic lactic acid bacterium that is capable of being transformed with an expression vector such as an anaerobe-derived plasmid having a gene for expressing a useful active protein introduced thereinto.

Furthermore, the present inventors have also investigated into an expression vector that functions in an obligately anaerobic lactic acid bacterium and found that an expression vector that comprises a *Lactobacillus*-derived plasmid replication protein gene (Rep), a secretion signal sequence (PslpA-SSartP) comprising a *Lactobacillus*-derived s-layer gene promoter and a *Lactobacillus*-derived PrtP protein secretion signal, and one or more selection marker genes is capable of an efficient transformation of an obligately anaerobic lactic acid bacterium and promoting a good protein expression and protein secretion.

As a result of further research based on the above-mentioned investigation results, the present invention has been accomplished.

Accordingly, the present invention relates to an obligately anaerobic lactic acid bacterium that has been mutated from being facultatively anaerobic to being obligately anaerobic so that the bacterium does not grow or has a very low growth rate in an aerobic environment but is capable of growing in an anaerobic environment.

Moreover, the present invention relates to the obligately anaerobic lactic acid bacterium, wherein the bacterium is capable of being transformed by an expression vector.

Furthermore, the present invention relates to the obligately anaerobic lactic acid bacterium, wherein the expression vector is an expression vector into which has been introduced a gene expressing a protein having activity useful for the treatment of a disease that is in an anaerobic environment.

Moreover, the present invention relates to the obligately anaerobic lactic acid bacterium, wherein the lactic acid bacterium is selected from the group consisting of a *Lactobacillus* genus bacterium, a *Streptococcus* genus bacterium, an *Enterococcus* genus bacterium, and a *Lactococcus* genus bacterium.

Furthermore, the present invention relates to the obligately anaerobic lactic acid bacterium, wherein the lactic acid bacterium is a *Lactobacillus* genus bacterium.

Moreover, the present invention relates to the obligately anaerobic lactic acid bacterium, wherein the *Lactobacillus* genus bacterium is selected from the group consisting of *Lactobacillus acidophilus, Lactobacillus gasseri, Lactobacillusjohnsonii, Lactobacillus helveticus, Lactobacillus salivarius, Lactobacillus delbrueckii, Lactobacillus plantarum, Lactobacillus casei, Lactobacillus rhamnosus, Lactobacillus reuteri*, and *Lactobacillus paracasei*.

Furthermore, the present invention relates to the obligately anaerobic lactic acid bacterium, wherein the *Lactobacillus* genus bacterium is *Lactobacillus casei*.

Moreover, the present invention relates to the obligately anaerobic lactic acid bacterium, wherein the *Lactobacillus casei* is *Lactobacillus casei* KK378 (NPMD (National Institute of Technology and Evaluation Patent Microorganisms Depositary) Accession No.: NITE BP-654) or a transformed bacterium thereof.

Furthermore, the present invention relates to the obligately anaerobic lactic acid bacterium, wherein the transformed bacterium of *Lactobacillus casei* KK378 is *Lactobacillus casei* KJ686 (Accession No.: NITE BP-615).

Moreover, the present invention relates to the obligately anaerobic lactic acid bacterium, wherein the transformed bacterium of *Lactobacillus casei* KK378 is *Lactobacillus casei* KJ474.

Furthermore, the present invention relates to an expression vector functioning in an obligately anaerobic lactic acid bacterium, the vector comprising a *Lactobacillus*-derived plasmid replication protein gene (Rep), a secretion signal sequence (PslpA-SSartP) comprising a *Lactobacillus*-derived s-layer gene promoter and a *Lactobacillus*-derived PrtP protein secretion signal, and one or more selection marker genes.

Moreover, the present invention relates to the expression vector, wherein the obligately anaerobic lactic acid bacterium is an obligately anaerobic lactic acid bacterium that has been mutated from being facultatively anaerobic to being obligately anaerobic so that the bacterium does not grow or has a very low growth rate in an aerobic environment but is capable of growing in an anaerobic environment.

Furthermore, the present invention relates to the expression vector, wherein the vector further comprises a desired protein-expressing gene downstream of the secretion signal sequence (PslpA-SSartP).

Moreover, the present invention relates to the expression vector, wherein the desired protein is a protein (A) having an antitumor activity and/or a protein (B) having activity of converting an antitumor substance precursor into an antitumor substance.

Furthermore, the present invention relates to the expression vector, wherein the protein (A) having an antitumor activity is a cytokine selected from the group consisting of interferons (IFNs)-α, β and γ, granulocyte macrophage colony stimulating factor (GM-CSF), interleukins (ILs)-1α, 1β, 2, 3, 4, 6, 7, 10, 12, 13, 15 and 18, tumor necrosis factor (TNF)-α, lymphotoxin (LT)-β, granulocyte colony stimulating factor (G-CSF), macrophage colony stimulating factor (M-CSF), macrophage migration inhibitory factor (MIF), leukemia inhibitory factor (LIF), T-cell activation costimulatory factors B7 (CD80) and B7-2 (CD86), KIT ligand, and Oncostatin M, and/or one type of angiogenesis inhibitor selected from the group consisting of endostatin, angiostatin, and kringles-1, 2, 3, 4 and 5.

Moreover, the present invention relates to the expression vector, wherein the protein (B) having an activity of converting an antitumor substance precursor into an antitumor substance is selected from the group consisting of cytosine deaminase, β-glucuronidase, and nitroreductase.

Furthermore, the present invention relates to the expression vector, wherein selection marker activity is one or more selected from drug resistance, auxotrophy, and medium selectivity.

Moreover, the present invention relates to the expression vector, wherein the drug resistance is one or more selected from the group consisting of erythromycin resistance, ampicillin resistance, tetracycline resistance, neomycin resistance, and kanamycin resistance.

Furthermore, the present invention relates to the expression vector, wherein the selection marker gene is one or two selected from a *Lactobacillus*-derived erythromycin resistance gene and an *Escherichia coli*-derived ampicillin resistance gene.

Moreover, the present invention relates to the expression vector, wherein the vector is plasmid pLPD8s or plasmid pLPD8s having any protein-expressing gene introduced thereinto.

Furthermore, the present invention relates to the obligately anaerobic lactic acid bacterium, the bacterium being transformed using any of the above expression vectors.

Moreover, the present invention relates to a pharmaceutical composition comprising as an active ingredient any one or more of the above obligately anaerobic lactic acid bacteria.

Furthermore, the present invention relates to an antitumor drug comprising a combination of the pharmaceutical composition comprising as an active ingredient the obligately anaerobic lactic acid bacterium, and a pharmaceutical composition comprising as an active ingredient an antitumor substance precursor that is converted into an antitumor substance by a protein (B) having activity of converting the antitumor substance precursor into the antitumor substance.

Moreover, the present invention relates to a method for preparing an obligately anaerobic lactic acid bacterium that has been mutated from being facultatively anaerobic to being obligately anaerobic so that the bacterium does not grow or has a very low growth rate in an aerobic environment, but is capable of grows in an anaerobic environment, the method comprising a step of (1) mutating a facultatively anaerobic wild-type lactic acid bacterium, and a step of (2) culturing the mutant bacterium under anaerobic conditions and under aerobic conditions, and selecting an obligately anaerobic mutant bacterium that grows only under the anaerobic conditions.

Furthermore, the present invention relates to the method for preparing an obligately anaerobic lactic acid bacterium, wherein the method further comprises a step of (3) transforming the obligately anaerobic mutant bacterium using an anaerobe-derived expression vector having one or more types of selection markers, and a step of (4) selecting from the transformed bacteria, by means of the selection marker, a transformed bacterium that has been transformed by the expression vector.

Moreover, the present invention relates to the method for preparing an obligately anaerobic lactic acid bacterium, wherein the mutation is chemical mutation by means of a mutagen.

Furthermore, the present invention relates to the method for preparing an obligately anaerobic lactic acid bacterium, wherein the mutagen is a nitrosoguanidine derivative.

Moreover, the present invention relates to the method for preparing an obligately anaerobic lactic acid bacterium, wherein the mutagen is N-methyl-N'-nitro-nitrosoguanidine (MNNG).

Furthermore, the present invention relates to the method for preparing an obligately anaerobic lactic acid bacterium, wherein the method employs any of the above expression vectors.

Moreover, the present invention relates to the method for preparing an obligately anaerobic lactic acid bacterium, wherein the facultatively anaerobic wild-type lactic acid bacterium is selected from the group consisting of a *Lactobacillus* genus bacterium, a *Streptococcus* genus bacterium, an *Enterococcus* genus bacterium, and a *Lactococcus* genus bacterium.

Furthermore, the present invention relates to the method for preparing an obligately anaerobic lactic acid bacterium, wherein the facultatively anaerobic wild-type lactic acid bacterium is a *Lactobacillus* genus bacterium.

Moreover, the present invention relates to the method for preparing an obligately anaerobic lactic acid bacterium, wherein the *Lactobacillus* genus bacterium is selected from the group consisting of *Lactobacillus acidophilus*, *Lactobacillus gasseri*, *Lactobacillus johnsonii*, *Lactobacillus helveticus*, *Lactobacillus salivarius*, *Lactobacillus delbrueckii*, *Lactobacillus plantarum*, *Lactobacillus casei*, *Lactobacillus rhamnosus*, *Lactobacillus reuteri*, and *Lactobacillus paracasei*.

Furthermore, the present invention relates to the method for preparing an obligately anaerobic lactic acid bacterium, wherein the *Lactobacillus* genus bacterium is *Lactobacillus casei*.

Moreover, the present invention relates to the method for preparing an obligately anaerobic lactic acid bacterium, wherein the *Lactobacillus casei* is *Lactobacillus casei* IGM393.

Since the obligately anaerobic lactic acid bacterium of the present invention specifically colonizes and grows in tumor tissue, etc. that is in an anaerobic environment, but quickly disappears from normal tissue that is in an aerobic environment and does not grow or has a very low growth rate; it does not act on tissue or organs other than the disease region and can only be made to act on the disease region that is in an anaerobic environment; and it is very useful as a therapeutic agent for a disease such as a malignant tumor that is in an anaerobic environment, as a gene transporting microorganism that can express a protein useful for the treatment of the disease, and as a parent bacterium therefor.

Moreover, surprisingly, the obligately anaerobic lactic acid bacterium of the present invention, for example, *Lactobacillus casei* KJ686, itself exhibits an antitumor effect.

Therefore, by combining the obligately anaerobic lactic acid bacterium of the present invention as an active ingredient, it is possible to produce an antitumor drug for which there is no possibility of side effects manifesting in normal tissue even in systemic administration such as intravenous injection, that does not put any restrictions on the method of administration, is very safe, and is easy to use.

Furthermore, by transforming the obligately anaerobic lactic acid bacterium of the present invention using an expression vector that functions in the lactic acid bacterium and has a any active protein-expressing gene inserted thereinto, it is possible to prepare a gene transporter that can express the any active protein. The gene transporter thus prepared can be expected to have multiple and synergistic effects from the effect of the action of the active protein in addition to the antitumor effect possessed by the bacterium itself, and can become an even more excellent antitumor drug.

Moreover, the obligately anaerobic lactic acid bacterium of the present invention can be transformed by the expression vector of the present invention, which is described later, such as, for example, pLPD8s, which is an *Escherichia coli*-*Lactobacillus* bacterium shuttle vector, or a vector in which a any protein-expressing gene has been introduced into pLPD8s such as, for example, pLPD8s::hIL-2, which is a vector into which a human IL-2-produced gene has been introduced; unlike *Bifidobacterium* genus bacteria transformed by a conventional expression vector these transformant bacteria transformed by the expression vector of the present invention is capable of extracellularly secreting a useful active protein produced by the expression gene. Therefore, by carrying out transformation by inserting a desired protein-expressing gene into the expression vector of the present invention, it is possible to prepare a gene transporter that secretes any active protein extracellularly.

As hereinbefore described, a transgenic vector in a lactic acid bacterium generally has high host specificity; the natural mutant type obligatory anaerobes reported so far do not allow an expression vector generally used for gene recombination of a lactic acid bacterium, such as a pLP400 series vector, to function, and it is necessary to develop an expression vector dedicated to the strain. On the other hand, unlike the natural mutant type obligatory anaerobes, the obligately anaerobic lactic acid bacterium of the present invention enables an expression vector generally used for gene recombination of a lactic acid bacterium to function therein.

That is, the obligately anaerobic lactic acid bacterium of the present invention is characterized in that it has been mutated from being facultatively anaerobic to being obligately anaerobic while maintaining its intrinsic function of being able to be transformed by a general expression vector.

Also encompassed herein are isolated obligately anaerobic lactic acid bacteria that do not grow or have a very low growth rate in an aerobic environment, e.g., about 0.1%, 0.2%, 0.5%; 0.1% to 1.0%; 0.1% to 2.0%; 0.1% to 3.0%; 0.1% to 4.0%; 0.1% to 5.0%; or 0.1% to 10%, of the growth rate or the amount of growth in an anaerobic environment, wherein the obligately anaerobic lactic acid bacterium is not a *Bifidobacterium*. In one aspect, the isolated obligately anaerobic lactic acid bacterium is non-naturally occurring. In a further aspect, the obligately anaerobic lactic acid bacterium comprises an expression vector that comprises a nucleic acid that encodes a protein having activity useful for the treatment of a disease that is in an anaerobic environment.

Also encompassed herein are isolated obligately anaerobic lactic acid bacteria comprising an expression vector, the vector comprising a *Lactobacillus*-derived plasmid replication protein gene (Rep), a secretion signal sequence (PslpA-SSartP) comprising a *Lactobacillus*-derived s-layer gene promoter and a *Lactobacillus*-derived PrtP protein secretion signal, and one or more selection marker genes.

In certain aspects, the obligately anaerobic lactic acid bacteria comprise a mutation that results in a switch from being facultatively anaerobic to obligately anaerobic, wherein the mutation comprises a deletion. In certain aspects, the switch from being facultatively anaerobic to obligately anaerobic is permanent.

Also encompassed herein are methods for treating solid tumors comprising administration of pharmaceutical compositions and/or therapeutic agents comprising an obligate anaerobic lactic acid bacterium described herein. In one aspect, the obligate anaerobic lactic acid bacterium comprises an expression vector described herein. In one aspect, the method results in a reduction in the size of the tumor; suppression of the growth of the tumor; inhibition of the proliferation of the tumor cells; reduction in the number of tumor cells; and/or a decrease in the viability of the tumor cells.

Effects of the Invention

The obligately anaerobic lactic acid bacterium of the present invention has the property of not growing or having a very low growth rate in an aerobic environment, but being capable of growing in animal tissue that is in an anaerobic environment. Furthermore, it also has the property of being able to be transformed by an expression vector.

Furthermore, the expression vector of the present invention has the properties of functioning in an obligately anaerobic lactic acid bacterium and an obligately anaerobic lactic acid bacterium that has been mutated from being facultatively anaerobic to being obligately anaerobic, and of being able to promote good protein expression and protein secretion.

Therefore, the obligately anaerobic lactic acid bacterium of the present invention is very useful as a therapeutic agent for a disease that is in an anaerobic environment such as a malignant tumor, or as a parent bacterium for a any gene transporter useful as a therapeutic agent for the disease, and the expression vector of the present invention is very useful as an expression vector for preparing the therapeutic agent and the gene transporter.

DETAILED DESCRIPTION OF THE INVENTION

Figure 1:
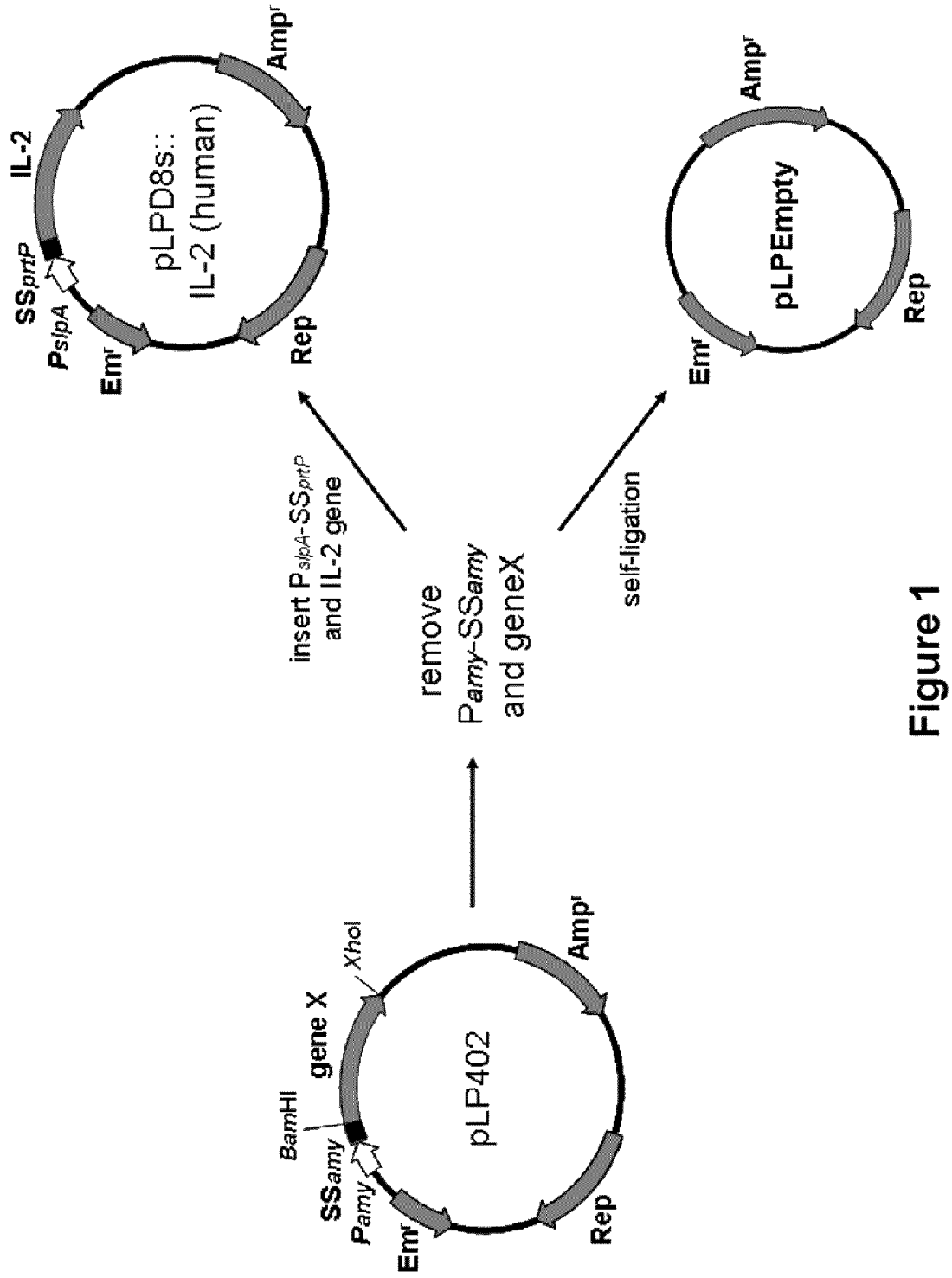
[FIG. 1] A map diagram showing the construction of plasmid vector pLPEmpty and plasmid vector pLPD8s::IL-2.

The lactic acid bacterium that has been mutated from being facultatively anaerobic to being obligately anaerobic of the present invention is nonpathogenic, has the property of not growing or having very low growth rate in an aerobic environment, and can have the property of being able to be transformed by an expression vector such as an anaerobe-derived plasmid into which has been introduced a gene for expressing a protein having activity useful for the treatment of a disease that is in an anaerobic environment. There are no particular restrictions as long as it is a lactic acid bacterium having the above-mentioned properties, and any species or strain is included.

The expression vector used for transformation of the lactic acid bacterium that has been mutated from being facultatively anaerobic to being obligately anaerobic of the present invention is not particularly limited as long as it is an expression vector that functions in a mutant lactic acid bacterium, and examples thereof include anaerobe-derived plasmids such as a lactic acid bacterium-derived plasmid, a fusion plasmid of a lactic acid bacterium-derived plasmid or part thereof and an *Escherichia coli*-derived plasmid or part thereof, and a lactic acid bacterium—*Escherichia coli* shuttle vector. Specific examples thereof include pLPD8s, which is a lactic acid bacterium—*Escherichia coli* shuttle vector and which is described later, and a vector having a any protein-expressing gene introduced into pLPD8s, such as pLPD8s::hIL-2, which is a vector having a human IL-2-produced gene introduced thereinto.

As the lactic acid bacterium that has been mutated from being facultatively anaerobic to being obligately anaerobic of the present invention, there can be cited various types of lactic acid bacteria used as probiotics, and examples thereof include *Lactobacillus* genus bacteria such as *Lactobacillus acidophilus, Lactobacillus gasseri, Lactobacillus johnsonii, Lactobacillus helveticus, Lactobacillus salivarius, Lactobacillus delbrueckii, Lactobacillus plantarum, Lactobacillus casei, Lactobacillus rhamnosus, Lactobacillus reuteri*, and *Lactobacillus paracasei, Streptococcus* genus bacteria such as *Streptococcus thermophilus, Enterococcus* genus bacteria such as *Enterococcus faecalis* and *Enterococcus faecium*, and *Lactococcus* genus bacteria such as *Lactococcus lactis*. Among these lactic acid bacteria, *Lactobacillus* genus bacteria are particularly preferable. Among the *Lactobacillus* genus bacteria, *Lactobacillus casei* is most preferable, and specific examples thereof include *Lactobacillus casei* KK378 (NPMD Accession No.: NITE BP-654).

As the obligately anaerobic lactic acid bacterium of the present invention that has been mutated from being facultatively anaerobic to being obligately anaerobic and further transformed, for example, obligately anaerobic lactic acid bacteria formed by transforming the above-mentioned various types of obligately anaerobic lactic acid bacteria can be cited, and specific examples thereof include *Lactobacillus casei* KJ686 (NPMD Accession No.: NITE BP-615) and *Lactobacillus casei* KJ474, which are transformant bacteria of *Lactobacillus casei* KK378.

The expression vector of the present invention is not particularly limited as long as it is an expression vector that functions in an obligately anaerobic lactic acid bacterium and contains a *Lactobacillus*-derived plasmid replication protein gene (Rep), a secretion signal sequence (PslpA-SSartP) comprising a *Lactobacillus*-derived s-layer gene promoter and a Lactobacillus-derived PrtP protein secretion signal, and one or more selection marker genes, but from the viewpoint of transformation efficiency, etc. there can be cited an expression vector in which the above-mentioned genes are introduced into a lactic acid bacterium-derived plasmid, a fusion plasmid of a lactic acid bacterium-derived plasmid or part thereof and an *Escherichia coli*-derived plasmid or part thereof, a lactic acid bacterium—*Escherichia coli* shuttle vector, etc.

Specific examples thereof include pLPD8s, which is a lactic acid bacterium—*Escherichia coli* shuttle vector, and a vector in which a any protein-expressing gene is introduced into the above, such as, for example, pLPD8s::hIL-2, which is a vector having introduced thereinto a human IL-2-produced gene.

pLPD8s is a vector that is an improvement of pLP402, which is conventionally used in the transformation of an anaerobe.

pLP402 is a vector having a *Lactobacillus*-derived plasmid replication protein gene (Rep), a *Lactobacillus*-derived erythromycin resistance gene ($Em^r$), an *Escherichia coli*-derived ampicillin resistance gene ($Amp^r$), an α-amylase gene promoter region and secretion signal sequence (Pamy-SSamy), and an inserted-gene expression sequence (BamHI-gene X-XhoI), and is a vector often used in transformation of a *Lactobacillus* genus bacterium, but has the defect that in a medium containing glucose as a sugar source, expression of recombinant protein is suppressed.

pLPD8s is constructed by removing the α-amylase gene promoter region and secretion signal sequence (Pamy-SSamy) and the inserted-gene expression sequence (BamHI-gene X-XhoI) of pLP402, and instead inserting a *Lactobacillus brevis*-derived promoter and an *L. casei* PrtP gene-derived secretion signal sequence (PslpA-SSprtP). This prevents the suppression of expression of recombinant protein even in a medium containing glucose as a sugar source and enables good protein expression and secretion to be promoted.

As the obligately anaerobic lactic acid bacteria in which the expression vector of the present invention functions, and the obligately anaerobic lactic acid bacteria transformed with the expression vector of the present invention, there can be cited obligately anaerobic lactic acid bacteria constructed by mutating from being facultatively anaerobic to being obligately anaerobic various types of lactic acid bacteria used as probiotics, such as *Lactobacillus* genus bacteria such as *Lactobacillus acidophilus*, *Lactobacillus gasseri*, *Lactobacillus johnsonii*, *Lactobacillus helveticus*, *Lactobacillus salivarius*, *Lactobacillus delbrueckii*, *Lactobacillus plantarum*, *Lactobacillus casei* *Lactobacillus rhamnosus*, *Lactobacillus reuteri*, and *Lactobacillus paracasei*, *Streptococcus* genus bacteria such as *Streptococcus thermophilus*, *Enterococcus* genus bacteria such as *Enterococcus faecalis* and *Enterococcus faecium*, and *Lactococcus* genus bacteria such as *Lactococcus lactis*.

Moreover, there can be cited obligately anaerobic lactic acid bacteria such as *Bifidobacterium* genus bacteria, for example, *Bifidobacterium adolescentis*, *Bifidobacterium animalis*, *Bifidobacterium infantis*, *Bifidobacterium thermophilum*, *Bifidobacterium pseudolongum*, *Bifidobacterium bifidum*, *Bifidobacterium breve*, and *Bifidobacterium longum*.

Among these lactic acid bacteria, *Bifidobacterium* genus bacteria and *Lactobacillus* genus bacteria that have been mutated from being facultatively anaerobic to being obligately anaerobic are preferable. Among the *Lactobacillus* genus bacteria, *Lactobacillus casei* is particularly preferable, and specific examples thereof include *Lactobacillus casei* KK378 (NPMD Accession No.: NITE BP-654). Among the *Bifidobacterium* genus bacteria, *Bifidobacterium longum* is particularly preferable.

Furthermore, with regard to a protein, coded by a gene of the expression vector of the present invention, having activity useful for the treatment of a disease that is in an anaerobic environment, active proteins useful for the treatment of various types of solid tumors include a protein having antitumor activity, a protein having activity of converting an antitumor substance precursor into an antitumor substance, etc., and active proteins useful for the treatment of an ischemic disease include a protein having angiogenic promoting activity, etc.

The protein having antitumor activity includes a cytokine, and specific examples thereof include interferons (IFNs)-α, β and γ, granulocyte macrophage colony stimulating factors (GM-CSFs), interleukins (ILs)-1α, 1β, 2, 3, 4, 6, 7, 10, 12, 13, 15 and 18, tumor necrosis factor (TNF)-α, lymphotoxin (LT)-β, granulocyte colony stimulating factor (G-CSF), macrophage colony stimulating factor (M-CSF), macrophage migration inhibitory factor (MIF), leukemia inhibitory factor (LIF), T-cell activation costimulatory factors B7 (CD80) and B7-2 (CD86), KIT ligand, and Oncostatin M.

Examples further include angiogenesis inhibitors such as endostatin, angiostatin, and kringles-1, 2, 3, 4 and 5.

Examples of the protein having activity of converting an antitumor substance precursor into an antitumor substance include cytosine deaminase (hereinafter, called CD), which is an enzyme converting 5-fluorocytosine (hereinafter, called 5-FC) into 5-fluorouracil (hereinafter, called 5-FU), which is an antitumor active substance, β-glucuronidase, which is an enzyme that converts various types of antitumor substance glucuronides into the antitumor substance, and nitroreductase, which is an enzyme that converts the antitumor substance precursor CB1954 into the antitumor substance.

When a synergistic effect can be expected, two or more genes coding for the above-mentioned proteins having antitumor activity and/or proteins having activity of converting an antitumor substance precursor into an antitumor substance may be combined and introduced.

Furthermore, the protein having angiogenic promoting activity includes various growth factors such as, for example, fibroblast growth factor 2 (FGF2), endothelial cell growth factor (ECGF), vascular endothelial growth factor (VEGF), hepatocyte growth factor (HGF), etc. When a synergistic effect can be expected, two or more genes coding for these active proteins may be combined and introduced.

A selection marker that is possessed by the expression vector of the present invention is not particularly limited as long as it is capable of confirming that the expression vector is functioning, and includes, for example, drug resistance, auxotrophy, medium selectivity, etc. From the viewpoint of convenience of operation, reliable selection, etc., drug resistance such as erythromycin resistance, ampicillin resistance, tetracycline resistance, neomycin resistance, or kanamycin resistance is preferable.

Furthermore, the expression vector of the present invention may have at least one selected from these selection markers.

The obligately anaerobic lactic acid bacterium of the present invention can be prepared by combining a standard mutation technique, gene transformation technique, cloning technique, etc.

Accordingly, an obligately anaerobic lactic acid bacterium that does not grow or has a very low growth rate in an aerobic environment but grows in an anaerobic environment can be prepared by carrying out following operations of: (1) mutating a wild-type lactic acid bacterium, and (2) culturing the mutant bacterium both under anaerobic conditions and under aerobic conditions, and selecting an obligately anaerobic mutant bacterium that only grows under anaerobic conditions.

Furthermore, an obligately anaerobic lactic acid bacterium, capable of being transformed with an expression vector such as an anaerobe-derived plasmid having introduced thereinto a gene for expressing a protein having activity useful for the treatment of a disease that is in an anaerobic environment, can be prepared by carrying out following operations of: (3) transforming the obligately anaerobic mutant bacterium using an expression vector having one or more types of selection markers, and (4) selecting from the transformant bacteria, by means of the selection marker, a transformant bacterium that is transformed by the expression vector.

A mutation method in operation (1) may be any mutation method as long as the mutation can impart the bacterium the property absent in a wild-type lactic acid bacterium that it does not grow or has a very low growth rate in an aerobic environment but grows in an anaerobic environment, while maintaining the property of a wild-type lactic acid bacterium that it is capable of being transformed with an expression vector such as an anaerobe-derived plasmid having introduced thereinto a gene for expressing a protein having activity useful for the treatment of a disease that is in an anaerobic environment. Examples of the mutation method include chemical mutation and exposure to radiation, and from the viewpoint of convenience of operation and the possibility of simultaneously mutating a plurality of sites without specifying in advance sites where each property is expressed, chemical mutation using a mutagen is preferable.

The mutagen used in chemical mutation is not particularly limited as long as it is a mutagen that imparts the abovementioned properties. A nitrosoguanidine derivative is preferable, and specific examples thereof include N-methyl-N'-nitro-nitrosoguanidine (MNNG).

The wild-type lactic acid bacterium used in preparation of the obligately anaerobic lactic acid bacterium of the present invention is not particularly limited as long as it is a nonpathogenic lactic acid bacterium, and any species or strain may be used. The bacterium may have both or either of the property of not growing or having a very low growth rate in an aerobic environment but growing in an anaerobic environment and the property of being able to be transformed with an expression vector such as an anaerobe-derived plasmid having introduced thereinto a gene for expressing a protein having activity useful for the treatment of a disease that is in an anaerobic environment.

As the wild-type lactic acid bacterium used in preparation of the obligately anaerobic lactic acid bacterium of the present invention, there can be cited lactic acid bacteria used as probiotics such as, for example, *Lactobacillus* genus bacteria such as *Lactobacillus acidophilus, Lactobacillus gasseri, Lactobacillusjohnsonii, Lactobacillus helveticus, Lactobacillus salivarius, Lactobacillus delbrueckii, Lactobacillus plantarum, Lactobacillus casei Lactobacillus rhamnosus, Lacto bacillus reuteri*, and *Lactobacillus paracasei, Streptococcus* genus bacteria such as *Streptococcus thermophilus, Enterococcus* genus bacteria such as *Enterococcus faecalis* and *Enterococcus faecium*, and *Lactococcus* genus bacteria such as *Lactococcus lactis*.

Among these lactic acid bacteria, the *Lactobacillus* genus bacteria are particularly preferable. Among the *Lactobacillus* genus bacteria, *Lactobacillus casei* is most preferable, and specific examples thereof include *Lactobacillus casei* IGM393.

All of these bacteria are commercially available or readily available from a depository institution.

The pharmaceutical composition of the present invention is not particularly limited as long as it contains the obligately anaerobic lactic acid bacterium of the present invention that has been mutated from being facultatively anaerobic to being obligately anaerobic, or a obligately anaerobic transformed lactic acid bacterium generated by further transforming the obligately anaerobic lactic acid bacterium with the expression vector of the present invention, etc. Furthermore, antitumor drug of the present invention is not particularly limited as long as it contains the obligately anaerobic lactic acid bacterium or the obligately anaerobic transformed lactic acid bacterium of the present invention.

The pharmaceutical composition or antitumor drug of the present invention may contain two or more the obligately anaerobic lactic acid bacterium and the obligately anaerobic transformant lactic acid bacterium of the present invention.

Moreover, the pharmaceutical composition and antitumor drug of the present invention may contain an optional component in addition to the obligately anaerobic lactic acid bacterium of the present invention as long as colonization, viability, and proliferation of the obligatory anaerobe of the present invention are not inhibited. Examples of such optional components include a pharmacologically acceptable carrier, diluent, suspending agent, pH adjusting agent, and cryoprotective agent. Furthermore, in order to promote the colonization, viability, and proliferation of the obligatory anaerobe, a pharmacologically acceptable bacterial nutrient, etc. may be contained.

The obligately anaerobic lactic acid bacterium, which is a main component of the pharmaceutical composition or antitumor drug of the present invention, has very high safety; the dosage of the pharmaceutical composition or antitumor drug of the present invention may be selected appropriately according to the administration route, the extent of the disease, and the body weight, age and gender of a patient, and it may be increased or decreased appropriately according to the degree of improvement.

The range of the dose is not particularly limited as long as it is an amount sufficient for the bacterium to grow in the tumor site and itself exhibit an effective antitumor activity, an amount sufficient for expressing an effective therapeutic dose of a protein having antitumor activity, or an amount sufficient for expressing an amount of protein that can convert an antitumor substance precursor into an effective therapeutic dose of an antitumor substance, but from the viewpoints of economy and preventing side effects as much as possible, it is preferable to use the minimum amount in a range that gives necessary antitumor activity.

For example, when it is used in practice, the dose is appropriately set according to antitumor activity exhibited by the obligately anaerobic lactic acid bacterium used itself, the type of protein having antitumor activity produced by the obligately anaerobic lactic acid bacterium used, the effective therapeutic dose of the antitumor substance converted from the antitumor substance precursor, the amount of the active protein produced by the obligately anaerobic lactic acid bacterium used, etc.

In the case of systemic administration by intravenous injection, since it is in particular necessary to reduce a risk such as an embolus due to a clump of bacteria, it is preferable to divide and inject a plurality of injections having a concentration as low as possible or infuse continuously by diluting with an appropriate fluid replacement. For example, in the case of an adult, cells of the obligately anaerobic lactic acid bacterium of the present invention are administered at $10^6$ to $10^{12}$ cfu per kg weight per day by dividing into 1 to 3 times, and preferably successively for 1 to 3 days. More specifically, 1 to 1000 mL per adult of a preparation containing cells of the obligately anaerobic lactic acid bacterium of the present invention at $10^4$ to $10^{10}$ cfu/mL is administered directly or by diluting with an appropriate fluid replacement, preferably dividing it into 1 to 3 times per day, and more preferably successively for 1 to 3 days.

Furthermore, in the case of local administration involving direct administration to tumor tissue, since it is necessary for bacterial cells to be administered to the entire tumor tissue, a high concentration injection is desirably administered at a plurality of positions of the tumor tissue. For example, in the case of an adult, cells of the obligately anaerobic lactic acid bacterium are administered at $10^6$ to $10^{12}$ cfu per kg weight once per day, and successively for 1 to 3 days as necessary. More specifically, 1 to 1000 mL per adult of a preparation containing cells of the obligately anaerobic lactic acid bacterium of the present invention at $10^4$ to $10^{10}$ cfu/mL is administered directly, preferably once per day, and successively for 1 to 3 days as necessary.

When it is confirmed that the bacteria in the tumor tissue disappear during the treatment period, the treatment is temporarily suspended, and the bacteria are then administered in the same manner.

When the obligately anaerobic lactic acid bacterium of the present invention has been introduced therein a gene that can express a protein having activity of converting an antitumor substance precursor into an antitumor substance, the pharmaceutical composition or antitumor drug of the present invention containing the obligately anaerobic lactic acid bacterium as an active ingredient may be used in a combination with an amount of antitumor substance precursor that can be converted into an effective amount of antitumor substance by the protein expressed by the obligately anaerobic lactic acid bacterium. This antitumor substance precursor may be contained in the pharmaceutical composition or antitumor drug containing the obligately anaerobic lactic acid bacterium of the present invention as an active ingredient, but as a pharmaceutical composition containing the antitumor substance precursor it is preferable for it to be used in a combination with the pharmaceutical composition or antitumor drug containing the obligately anaerobic lactic acid bacterium of the present invention as an active ingredient.

The dose of the antitumor substance precursor may be selected appropriately depending on the growth rate in the tumor tissue of the obligately anaerobic lactic acid bacterium used in combination, the ability of the obligately anaerobic lactic acid bacterium to produce an active protein that converts the antitumor substance precursor into the antitumor substance, and the conversion rate from the antitumor substance precursor into the antitumor substance. Moreover, the dose of the obligately anaerobic lactic acid bacterium may be selected appropriately depending on the administration route, the extent of the disease, or the weight, age, and gender of a patient, and it may be increased or decreased appropriately according to the degree of improvement.

As described above, when the pharmaceutical composition or antitumor drug of the present invention is used in a combination with an antitumor substance precursor, the method for administering the pharmaceutical composition or antitumor drug of the present invention may be the same as or different from the method for administering the pharmaceutical composition containing the antitumor substance precursor, and administration may be at the same time or at separate times, but it is preferable that administration of the pharmaceutical composition containing the antitumor substance precursor is carried out after administration of the pharmaceutical composition or antitumor drug of the present invention, that is, after a time for the obligately anaerobic lactic acid bacterium of the present invention to grow sufficiently in the tumor cells has passed.

'A combination of X and Y' referred to in the present invention includes a case in which X and Y are in different configurations and a case in which X and Y are in the same configuration (e.g. a configuration containing X and Y). Furthermore, in the case in which X and Y are in different configurations, a case in which both X and Y may contain another component is also included.

The form of the pharmaceutical composition or antitumor drug of the present invention is not particularly limited, and examples thereof include a liquid formulation or a solid formulation containing the obligately anaerobic lactic acid bacterium of the present invention. The liquid formulation may be produced by purifying a culture fluid of the obligately anaerobic lactic acid bacterium of the present invention, adding thereto as necessary an appropriate physiological saline or fluid replacement, or a pharmaceutical additive, and charging into an ampoule, a vial container, etc. In a case of such a liquid formulation, it may be put in frozen storage as it is or put in frozen storage after adding an appropriate cryoprotective agent and freezing.

Furthermore, the solid formulation may be produced by adding an appropriate protective agent to a liquid formulation, charging into an ampoule, a vial container, etc., and then freeze drying or L-drying, or by adding an appropriate protective agent to a liquid formulation, freeze drying or L-drying, and then charging into an ampoule, a vial container, etc.

As a method for administering the pharmaceutical composition or antitumor drug of the present invention, parenteral administration is preferable; for example, subcutaneous injection, intravenous injection, local infusion, intracerebroventricular administration, etc. may be carried out, and intravenous injection is the most preferable.

The pharmaceutical composition or antitumor drug of the present invention may be applied to a tumor having an anaerobic environment, and preferably various types of solid cancers. Examples of the solid cancer include large bowel cancer, brain tumor, head and neck cancer, breast cancer, lung cancer, esophageal cancer, stomach cancer, liver cancer, gallbladder cancer, bile duct cancer, pancreatic cancer, islet cell cancer, chorionic cancer, colonic cancer, renal cell cancer, adrenal cortex cancer, bladder cancer, testicular cancer, prostate cancer, testicular tumor, ovarian cancer, uterine cancer, thyroid cancer, malignant carcinoid tumor, skin cancer, malignant melanoma, osteosarcoma, soft tissue sarcoma, neuroblastoma, Wilms' tumor, retinoblastoma, melanoma, and squamous cancer.

Examples of other diseases that are in an anaerobic environment include ischemic diseases such as cardiac infarction or arteriosclerosis obliterans, and lower limb ischemic disease such as Buerger's disease.

EXAMPLES

The present invention is explained more specifically below by reference to Examples and Test Examples, but the technical scope of the present invention is not limited by these exemplifications, and various modifications are possible as long as they do not depart from the technical spirit of the present invention.

Example 1

Preparation of Obligately Anaerobic Mutant Bacterium (*Lactobacillus casei* KK378 Strain)

*Lactobacillus case* IGM393 was added to MRS medium at a concentration of 1:100 and cultured overnight at 37° C. under anaerobic conditions; culturing was stopped when the turbidity ($OD_{600}$) at 600 nm became about 0.1, and 10 mL of the culture fluid was centrifuged at a rotational speed of 3000 G for 10 minutes, thus collecting cultured bacteria.

The cultured bacteria were washed with about 15 times the amount of 0.1 M potassium phosphate buffer (pH=7) and suspended in the same amount of the same buffer, 170 μg/mL of MNNG (N-methyl-N'-nitro-nitrosoguanidine) was added to this suspension, stirring was carried out at 37° C. for 20 minutes, the suspension was then immediately centrifuged at a rotational speed of 3000 G for 2 minutes, and washing with an appropriate amount of 0.1 M potassium phosphate buffer (pH=7) was carried out twice.

The washed bacterial liquid was suspended in 50 mL of MRS medium containing 0.05% of L-cysteine and cultured at 37° C. under anaerobic conditions for about 9 hours.

The cultured bacterial liquid was sown on MRS medium containing 0.05% of L-cysteine at about 300 colonies per plate, and cultured under anaerobic conditions.

Each colony was transplanted onto two plates, which were cultured separately under anaerobic conditions and under aerobic conditions, and colonies that only grew under anaerobic conditions were selected, thus obtaining an obligately anaerobic mutant *Lactobacillus casei* KK378 strain (NPMD Accession No.: NITE BP-654).

Example 2

Transformation of *Lactobacillus casei* KK378 Strain
(1)

(Preparation of Plasmid Vector pLPEmpty)

As shown in FIG. 1, an α-amylase gene promoter region and secretion signal sequence (Pamy-SSamy), and an inserted-gene expression sequence (BamHI-gene X-XhoI) were removed by a standard method from plasmid pLP402, which is generally used in transformation of *Lactobacillus genus* bacterium, thus preparing plasmid vector pLPEmpty.

The meanings of the reference symbols in the plasmid vector pLPEmpty map are as follows.

Amp$^r$: *Escherichia coli*-derived ampicillin resistance gene
Rep: *Lactobacillus*-derived plasmid replication protein gene
Em$^r$: *Lactobacillus*-derived erythromycin resistance gene
(Transformation)

The obligately anaerobic *Lactobacillus casei* KK378 strain, obtained in Example 1 above, was subjected to transformation by a standard method using the plasmid vector pLPEmpty obtained above, thus giving the obligatory anaerobe *Lactobacillus casei* KJ686 (NPMD Accession No.: NITE BP-615).

When the *Lactobacillus casei* KJ686 strain obtained above was cultured in a medium with added erythromycin, it was confirmed that the strain was an erythromycin resistant bacterium that could be grown in this selective medium, that is, it was transformed by plasmid vector pLPEmpty having the erythromycin resistance gene.

It can be seen from the results of Examples 1 and 2 above that the *Lactobacillus casei* KK378 bacterium was mutated from being facultatively anaerobic to being obligately anaerobic while maintaining the function of being able to be transformed by a plasmid generally used for transformation of a *Lactobacillus* genus bacterium.

Example 3

Preparation of Plasmid Vector PLPD8s::hIL-2

As in Example 2, as shown in FIG. 1, the a-amylase gene promoter region and secretion signal sequence (Pamy-SSamy), and the inserted-gene expression sequence (BamHI-gene X-XhoI) were removed from pLP402 by a standard method, and instead of these a *Lactobacillus brevis*-derived promoter and an *L. casei* PrtP gene-derived secretion signal sequence (PslpA-SSprtP) were inserted, thus preparing plasmid vector pLPD8s.

Separately therefrom, human IL-2 gene was amplified from a plasmid containing cDNA coding for human IL-2 (hIL-2) by a PCR method using a primer (CCC CGG ATC CGA GTG CAC CTA CTT CAA GTT C (SEQ ID: 5), and CCC CCT CGA GTC AAG TTA GTG TTG AGA TGA (SEQ ID: 6)).

This gene fragment was digested by BamHI and XhoI restriction enzymes, thus preparing a human IL-2 gene expression sequence (BamHI-IL-2gene-XhoI), and the sequence was inserted into a restriction enzyme site downstream of the secretion signal sequence (PslpA-SSprtP) of the plasmid vector pLPD8s, thus preparing plasmid vector pLPD8s::hIL-2.

The entire base sequence of the plasmid vector pLPD8s::hIL-2 is given in SEQ ID NO: 1 of the sequence listing. Furthermore, within pLPD8s::hIL-2, the base sequence of the *Lactobacillus*-derived plasmid replication protein gene (Rep) is given in SEQ ID NO:2 of the sequence listing, base sequences of the *Lactobacillus brevis*-derived promoter and the *L. casei* PrtP gene-derived secretion signal sequence (PslpA-SSprtP) are given in SEQ ID NO:3 of the sequence listing, and the base sequence of the human IL-2 gene expression sequence (BamHI-IL-2gene-XhoI) is given in SEQ ID NO:4 of the sequence listing.

Example 4

Transformation of *Lactobacillus casei* KK378 Strain
(2)

The obligately anaerobic *Lactobacillus casei* KK378 strain obtained in Example 1 above was subjected to transformation by a standard method using plasmid vector pLPD8s::hIL-2 obtained in Example 3 above, thus giving human IL-2 expression/secretion strain *Lactobacillus casei* KJ474.

Test Example 1

Test for ascertaining obligate anaerobicity of *Lactobacillus casei* KJ686 bacteria

*Lactobacillus casei* KJ686 bacteria obtained in Example 2 were applied on 2 MRS medium plates and they were cultured for 3 days, one at 37° C. under anaerobic conditions, and the other at 37° C. under aerobic conditions.

Results

Figure 2:
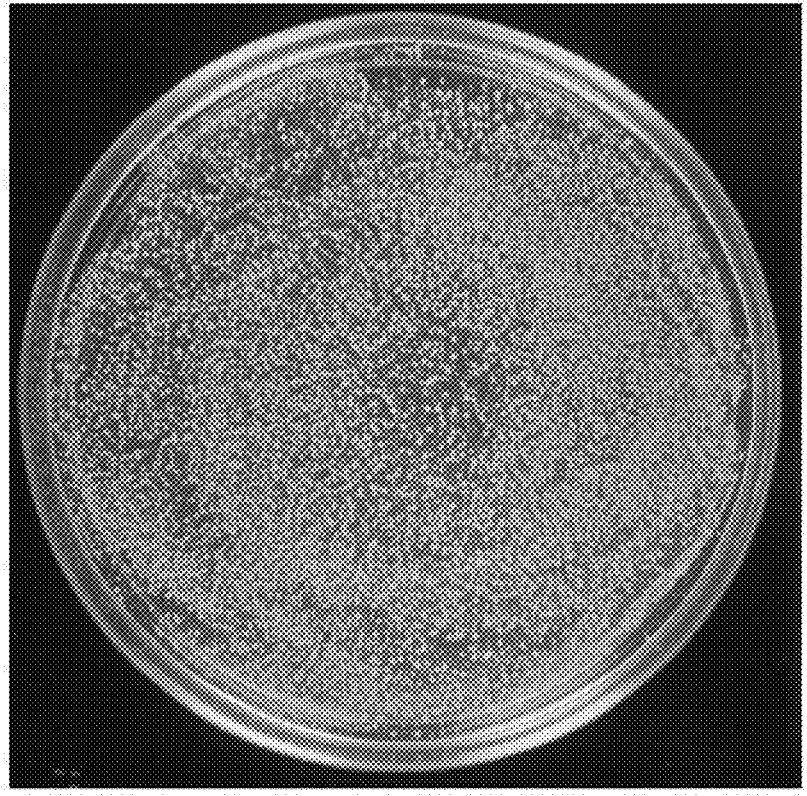
[FIG. 2] A photograph showing the results of KJ686 bacteria being cultured on an MRS medium plate at 37° C. under anaerobic conditions and under aerobic conditions.
Figure 2:
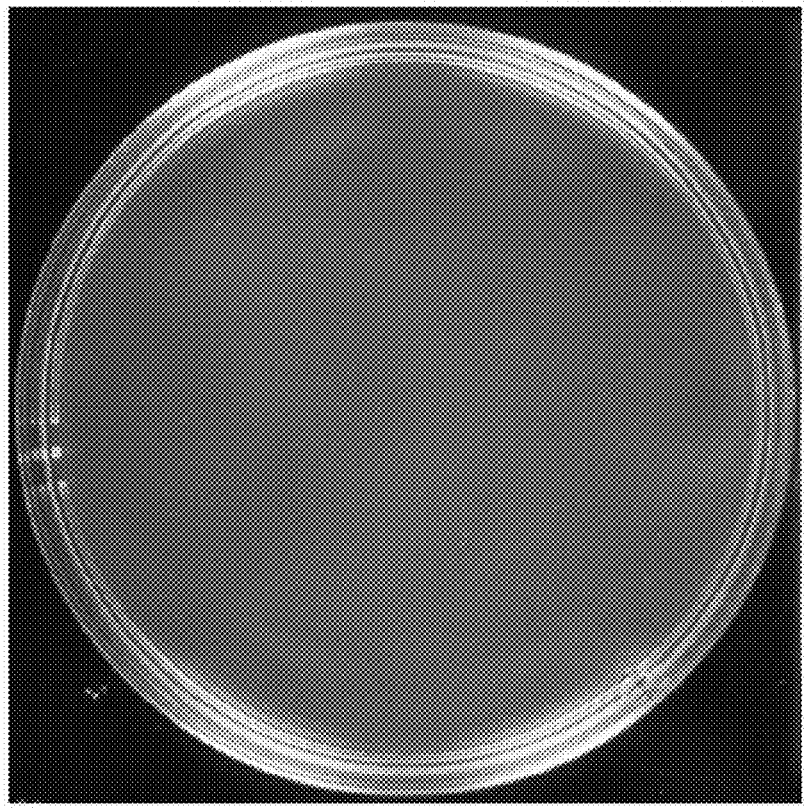

As shown in FIG. 2, the plate cultured under anaerobic conditions showed growth of the bacteria, whereas the plate cultured under aerobic conditions did not show any bacterial growth at all, thus confirming that *Lactobacillus casei* KJ686 is an obligatory anaerobe.

Test Example 2

Test for ascertaining tumor specific accumulation of *Lactobacillus casei* KJ686 bacteria

*Lactobacillus casei* KJ686 bacteria obtained in Example 2 were cultured in MRS medium under anaerobic conditions, and the cultured bacteria ($5 \times 10^9$/0.5 mL PBS) were intravenously administered to four B16F melanoma tumor-bearing mice. Three out of the four were sacrificed 96 hours after administration of the bacteria (after 4 days), and the remaining one was sacrificed 168 hours after administration of the bacteria (after 7 days), tumor tissue and normal tissue (liver, lung, kidney, blood) were removed and homogenized, and each tissue extract was applied on an MRS plate and cultured at 37° C. under anaerobic conditions for 3 days.

Results

In the case of 96 hours after administration of the bacteria (after 4 days), as shown in Table 1, it was ascertained that 2 cases out of the 3 cases showed survival of the bacteria within the tumor tissue, and the number of bacteria within the tumor was about $7.4 \times 10^5$ to $1.6 \times 10^6$ cfu/g. It was ascertained that 1 case out of the 3 cases also showed the presence of the bacteria in normal tissue.

In the case of 168 hours after administration of the bacteria (after 7 days), as shown in Table 2, it was ascertained that the bacteria were only in the tumor tissue, and the number of bacteria within the tumor was $5.2 \times 10^6$ cfu/g.

TABLE 1

| Sample No. | Tumor tissue | Lung | Liver | Kidney | Blood |
|---|---|---|---|---|---|
| Mouse (1) | $7.44 \times 10^5$ | 0 | 0 | 0 | 0 |
| Mouse (2) | 8 | 0 | 0 | 0 | 0 |
| Mouse (3) | $1.61 \times 10^6$ | 10 | 170 | Many | 10 |

TABLE 2

| Sample No. | Tumor tissue | Lung | Liver | Kidney | Blood |
|---|---|---|---|---|---|
| Mouse (4) | $5.2 \times 10^6$ | 0 | 0 | 0 | 0 |

Test Example 3

Test of antitumor activity of *Lactobacillus casei* KJ686 bacteria

Lewis lung carcinoma (LLC) cells ($1 \times 10^6$/50 µL) were transplanted under the skin of the right inguinal region of 8 week-old C57BL/6 mice, thus forming LLC tumor-bearing C57BL/6 mice.

Among 18 mice having a tumor diameter of about 5 mm, 8 randomly selected mice were intravenously administered with cultured bacteria ($5 \times 10^8$/100 µL) obtained by culturing in MRS medium under anaerobic conditions *Lactobacillus casei* KJ686 bacteria obtained in Example 2 (bacterial administration group). The remaining 10 mice were not treated (control group).

The tumor size was measured every day from the day the test was started (bacterial administration date), the point when the size of the tumor exceeded by about 20 times the size of the tumor when the test was started (when bacteria were administered) was defined as the end point, all of the mice of each group were sacrificed on the same day for each group, and the size of the tumor was measured. Furthermore, the tumor tissue and normal tissue (liver, lung) were removed and homogenized, and each tissue extract was applied on an MRS plate and cultured at 37° C. under anaerobic conditions for 3 days.

Results

Figure 3:
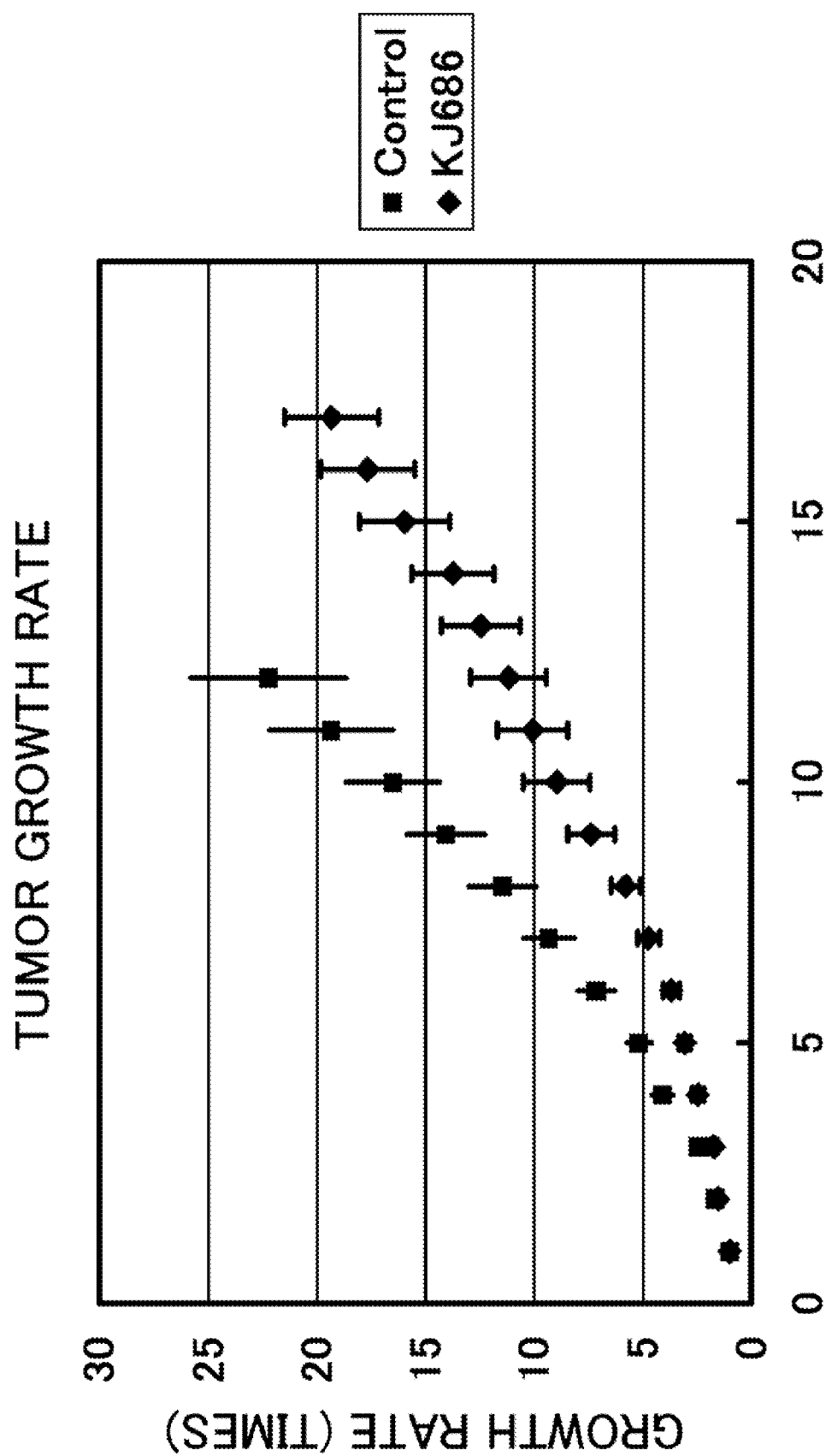
[FIG. 3] A graph showing the effect of KJ686 bacteria in reducing tumor proliferation in LLC tumor-bearing C57BL/6 mice. The ordinate denotes tumor growth rate (times) and the abscissa denotes the number of days.

As shown in a graph (FIG. 3) in which the tumor growth rate (times) is shown as an index where the size of the tumor when the test started (when bacteria were administered) is defined as 1, for the control group (untreated) the tumor increased by about 9 times in 7 days after the test was started, and up to about 23 times in 12 days, whereas for the bacterial administration group the tumor increased by about 5 times in 7 days after the bacteria were administered, about 11 times in 12 days, and about 20 times in 17 days, and it was confirmed that administration of the bacteria showed an apparent effect in suppressing the growth of the tumor.

Figure 4:
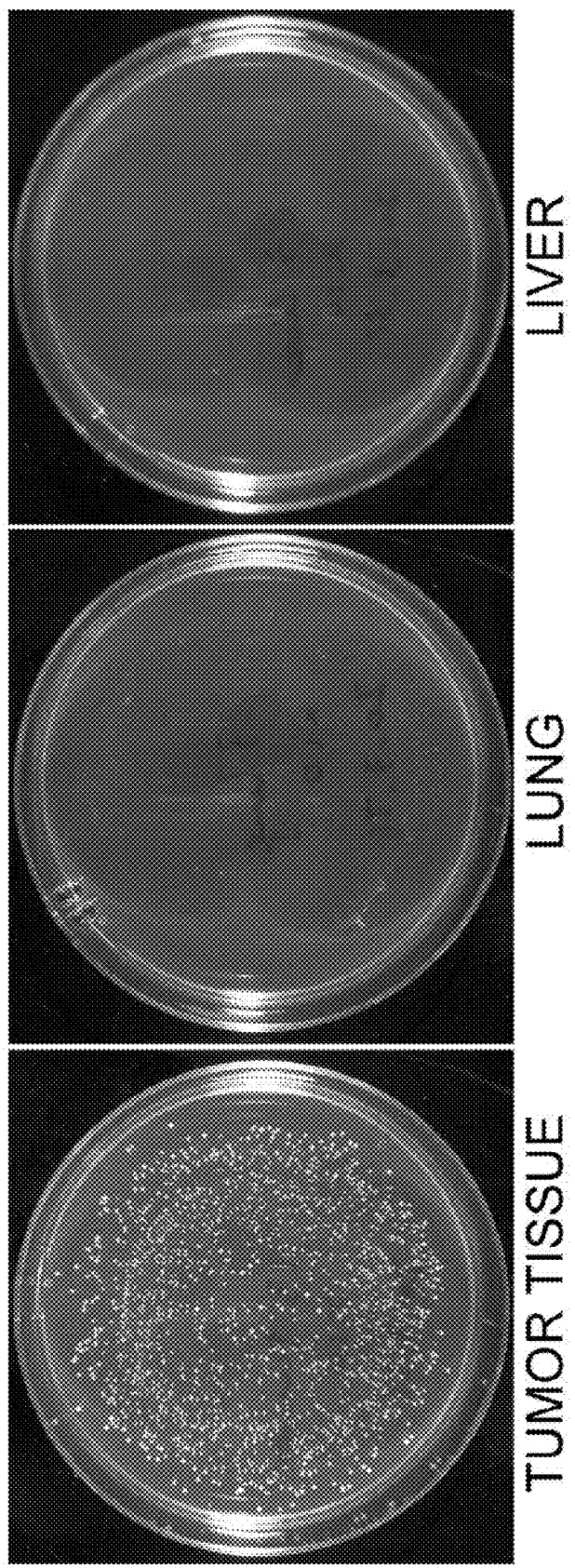
[FIG. 4] A photograph showing the results of KJ686 bacteria being administered via a tail vein to an LLC tumor-bearing C57BL/6 mouse successively for 2 days, removing tumor tissue and normal tissue (lung and liver) at the end point (when the tumor attained a diameter of 17 ram) and homogenizing, applying each tissue extract liquid on an MRS plate, and culturing at 37° C. under anaerobic conditions for 3 days.

Furthermore, as shown in FIG. 4, at a time of 17 days after administration of the bacteria, the bacteria only accumulated in the tumor tissue, and it was confirmed that the bacteria did not accumulate in normal tissue (lung and liver) at all.

Test Example 4

Test for ascertaining ability of *Lactobacillus casei* KJ474 bacterium to produce human IL-2

The ability of *Lactobacillus casei* KJ474 bacteria obtained in Example 4 to produce IL-2 was ascertained as follows.

The *Lactobacillus casei* KJ474 bacteria were cultured in a 5 µg/mL erythromycin-containing MRS liquid medium at 37° C. for 24 hours. 1 mL of the culture fluid was transferred to a 1.5 mL microtube and centrifuged at 13,000 rpm for 2 minutes, and 0.5 mL of supernatant was transferred to a new microtube.

1 mL of cold acetone was added to the culture supernatant and mixed, the mixture was centrifuged at 13,000 rpm for 30 minutes, and the supernatant was completely removed.

A precipitate was dissolved in 50 µL of SDS-PAGE sample buffer (10 times concentrated sample), thus giving a sample solution.

10 µL of the sample solution was subjected to SDS-PAGE (gel concentration 15%), and after electrophoresis was completed, protein was transferred onto a nitrocellulose membrane by electroblotting.

The protein on the nitrocellulose membrane was bound to anti-goat HRP secondary antibody using biotinylated anti-human IL-2 antibody as a primary antibody, and a photographic film was exposed.

*Lactobacillus casei* KJ686 bacteria to which the human IL-2 gene had not been introduced were tested at the same time as a negative control.

Results

Figure 5:
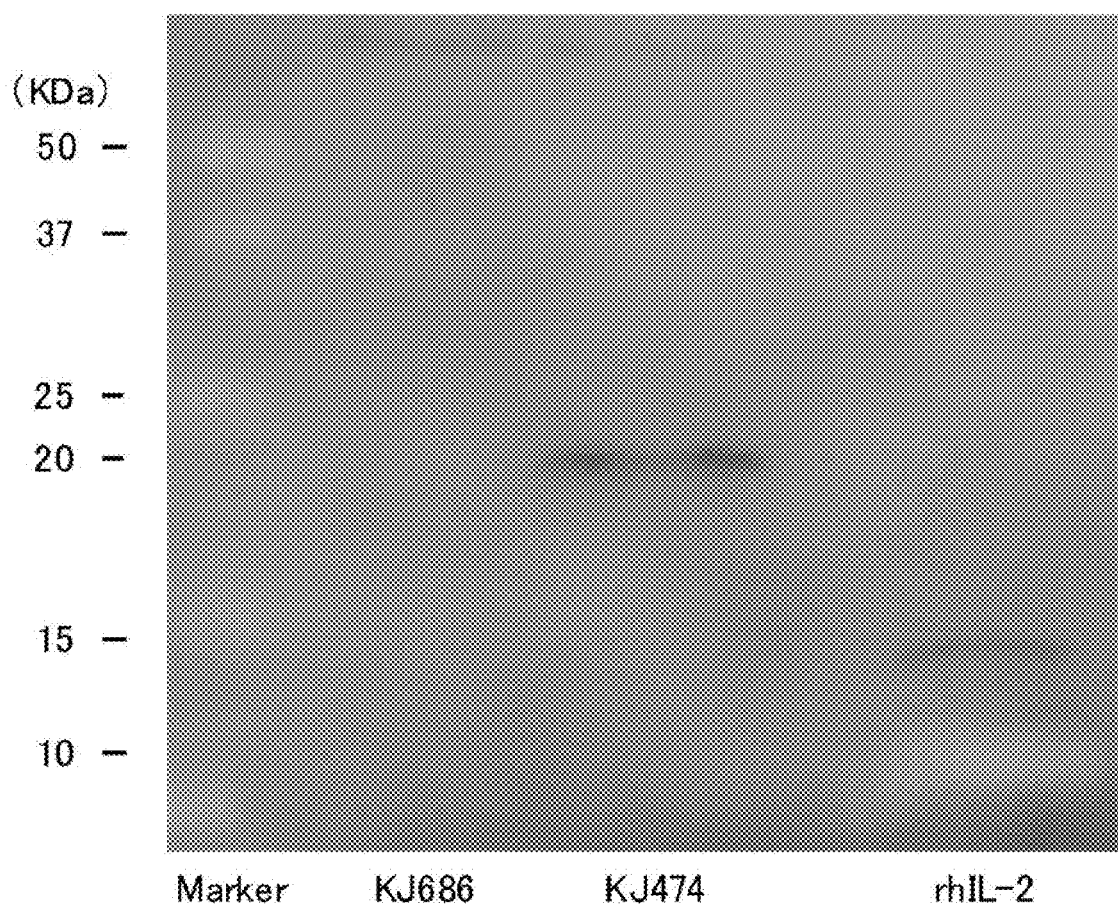
[FIG. 5] A diagram of electrophoresis of culture supernatant of KJ474 bacteria. Ordinate values denote molecular weight (kDa).

As shown in FIG. 5, from the electrophoresis of the culture supernatant of *Lactobacillus casei* KJ474 bacteria it was confirmed that *Lactobacillus casei* KJ474 bacterium produced human IL-2.

The difference in molecular weight between the protein produced by *Lactobacillus casei* KJ474 bacteria and an authentic human IL-2 preparation is due to a PrtP secretion signal sequence-derived peptide being added to the N terminal of IL-2 expressed by the KJ474 bacteria.

Test Example 5

Quantitative analysis of amount of human IL-2 produced by *Lactobacillus casei* KJ474 bacteria

*Lactobacillus casei* KJ474 bacteria cryopreserved at −80° C. were warmed to 37° C., and 5 µL thereof was cultured in 4 mL of a 5 µg/mL erythromycin-containing MRS liquid medium in an anaerobic environment at 37° C. for 24 hours.

Furthermore, 5 µL thereof was added to 4 mL of a 5 µg/mL erythromycin-containing MRS liquid medium and cultured in an anaerobic environment at 37° C. for 24 hours, the culture fluid was then centrifuged at 12000 rpm for 3 minutes, and culture supernatant was sampled and preserved at −80° C.

This culture fluid was diluted by 100,000 times, 100 µL thereof was applied to a 5 µg/mL erythromycin-containing MRS agar medium and cultured in an anaerobic environment at 37° C. for 3 days; the number of colonies was then counted, and it was found to be $4.8 \times 10^8$ cfu/mL.

Quantitative analysis of human IL-2 was carried out using a DuoSet ELISA development Human DY202 kit from R&D Systems.

When ELISA was carried out by diluting the culture supernatant by 1000 times, the result was 80.3 pg/mL. From the above, the actual amount of human IL-2 produced was calculated as 80.3 ng/mL with a dilution ratio of 1000 times when the number of bacteria in the *Lactobacillus casei* KJ474 bacterium culture fluid was defined as $4.8 \times 10^8$ cfu/mL.

Test Example 6

Evaluation of biological activity of human IL-2 produced by *Lactobacillus casei* KJ474 bacteria Evaluation of the biological activity of IL-2 was carried out using IL-2-dependent mouse T cells (CTLL-2).

$1 \times 10^4/100$ µL of CTLL-2 was sampled on a 96-well plate, and PBS (−) and 0.1% BSA were added to make a total amount of 112.5 µL. 1.5 ng/mL of transgenic human IL-2 (Product No. 202-IL) from R&D SYSTEMS was added thereto, and the proliferation rate of CTLL-2 was compared with one to which, instead of IL-2 above, a *Lactobacillus casei* KJ474 bacterial ($2.9 \times 10^9$ cfu) culture supernatant (10 times concentration) was added. The CTLL-2 cell count was measured with a WST-1 using MK400 colorant.

It was found that the one to which 1.5 ng/mL of transgenic human IL-2 (Product No. 202-IL) had been added proliferated by about 1.32 times, and one to which the *Lactobacillis casei* KJ474 bacterial culture supernatant (10 times concentration) had been added proliferated by about 1.52 times.

When the titer of human IL-2 was determined by conversion of the biological activity of human IL-2 produced by *Lactobacillus casei* KJ474 bacteria using the proliferation rate, the number of bacteria, and the concentration ratio, the calculation was as follows.

KJ474 bacteria produced hIL-2 1 ng=rhIL-2 $3.6 \times 10^{-4}$ ng
KJ474 bacteria $1 \times 10^9$ c.f.u.=rhIL-2 $6.0 \times 10^{-4}$ ng Test Example 7

Test of antitumor activity of *Lactobacillus casei* KJ474 bacteria

In the same manner as in Test Example 3, Lewis lung carcinoma (LLC) cells ($1 \times 10^6/50$ µL) were transplanted under the skin of the right inguinal region of 8 week-old C57BL/6 mice, thus forming LLC tumor-bearing C57BL/6 mice.

Among 18 mice having a tumor diameter of about 5 mm, 8 randomly selected mice were intravenously administered with cultured bacteria ($5 \times 10^8/100$ µL) obtained by culturing in MRS medium under anaerobic conditions *Lactobacillus casei* KJ474 bacteria obtained in Example 2 (bacterial administration group). The remaining 10 mice were not treated (control group).

The tumor size was measured every day from the day the test was started (bacterial administration date), the point when the size of the tumor exceeded by about 20 times the size of the tumor when the test was started (when bacteria were administered) was defined as the end point, all of the mice of each group were sacrificed on the same day for each group, and the size of the tumor was measured. Furthermore, the tumor tissue and normal tissue (liver, lung) were removed and homogenized, and each tissue extract was applied on an MRS plate and cultured at 37° C. under anaerobic conditions for 3 days.

Results

Figure 6:
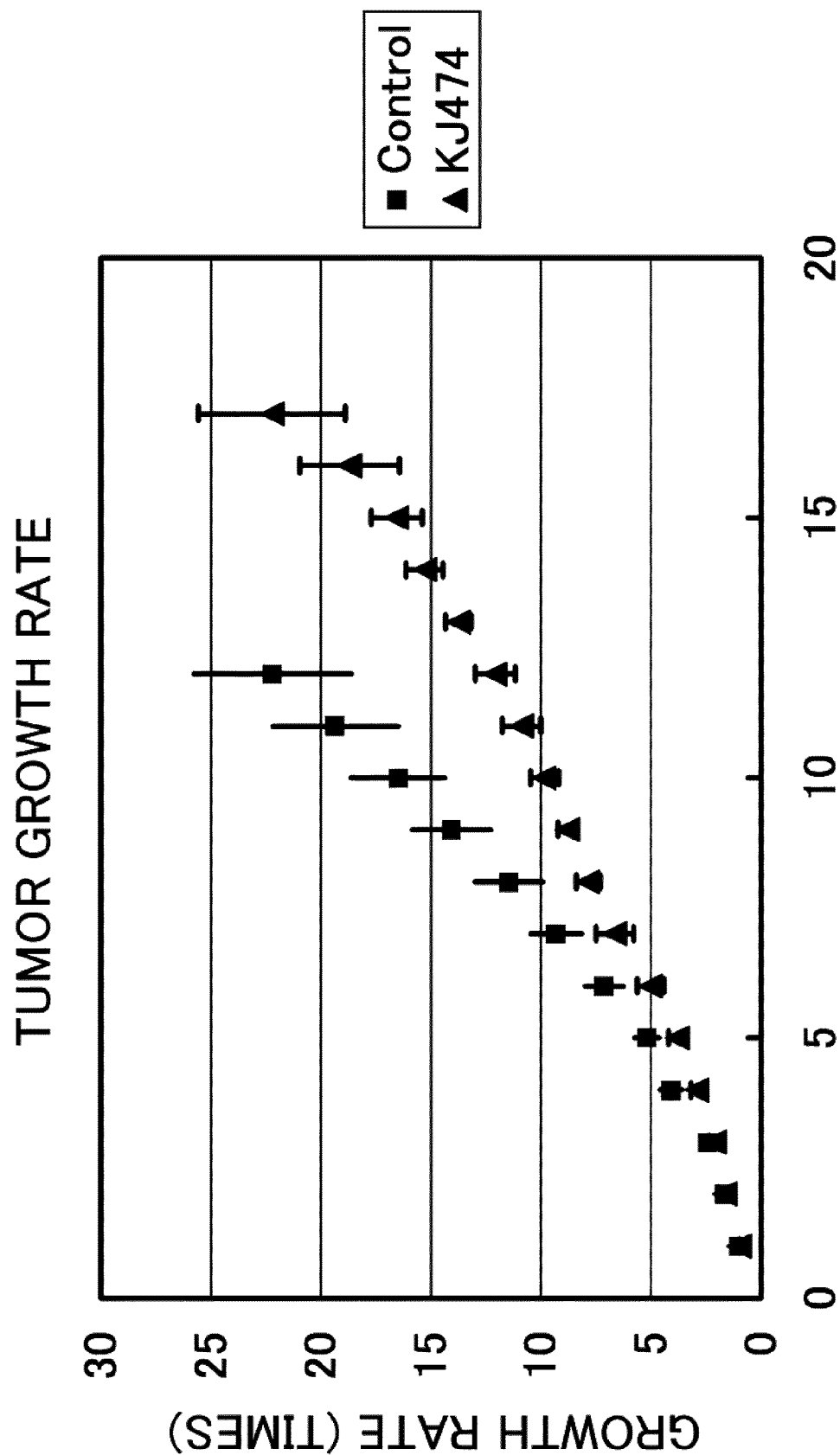
[FIG. 6] A graph showing the effect of KJ474 bacteria in reducing tumor proliferation in LLC tumor-bearing C57BL/6 mice. The ordinate denotes tumor growth rate (times) and the abscissa denotes the number of days.

As shown in a graph (FIG. 6) in which the tumor growth rate (times) is shown as an index where the size of the tumor when the test started (when bacteria were administered) is defined as 1, for the control group (untreated) the tumor increased by about 9 times in 7 days after the test was started, and about 23 times in 12 days, whereas for the bacterial administration group the tumor increased by about 6 times in 7 days after the bacteria were administered, about 12 times in 12 days, and finally about 23 times in 17 days, and it was confirmed that administration of the bacteria showed an apparent effect in suppressing the growth of the tumor.

Comparing the results of the test of the antitumor activity of *Lactobacillus casei* KJ474 bacteria with the above-mentioned results of the test of the antitumor activity of *Lactobacillus casei* KJ686 bacteria, there was no clear difference between the results. It is surmised that, since the tests were carried out by administering to mice *Lactobacillus casei* KJ474 bacteria transformed by introducing a gene for expressing human IL-2, the produced human IL-2 could not function sufficiently on the mouse cell immune system, etc., and an antitumor effect due to activation of the immune system, etc. could not be obtained. It is therefore surmised that by administering to a human *Lactobacillus casei* KJ474 bacteria transformed by introducing a gene for expressing human IL-2, a clearer and higher antitumor effect can be expected.

Industrial Applicability

The obligately anaerobic lactic acid bacterium of the present invention is nonpathogenic and has the property of not growing or having very low growth rate in an aerobic environment, and can have the property of being able to be transformed by an expression vector such as an anaerobe-derived plasmid into which has been introduced a gene for expressing a protein having activity useful for the treatment of a disease that is in an anaerobic environment.

Furthermore, the expression vector of the present invention functions in an obligately anaerobic lactic acid bacterium or an obligately anaerobic lactic acid bacterium that has been mutated from being facultatively anaerobic to being obligately anaerobic, and an obligately anaerobic lactic acid bacterium transformed by the vector of the present invention has the property of efficiently producing a protein having activity useful for the treatment of a disease that is in an anaerobic environment and secreting the active protein extracellularly.

Moreover, when intravenously administered to a tumor-bearing animal, the obligately anaerobic lactic acid bacterium of the present invention and the obligately anaerobic lactic acid bacterium transformed by the expression vector of the present invention, etc., specifically accumulate only in the tumor tissue, do not accumulate or hardly accumulate in normal tissue and, furthermore, exhibit an outstanding effect in suppressing growth of the tumor.

The obligately anaerobic lactic acid bacterium of the present invention is therefore very useful as a therapeutic agent for a disease such as a solid tumor that is in an anaerobic environment or as a parent bacterium for a gene transporter as a therapeutic agent for a disease that is in an anaerobic environment that can express a protein having activity useful for the treatment of a disease that is in an anaerobic environment and, moreover, the expression vector of the present invention is very useful as an expression vector for preparing the therapeutic agent and the gene transporter.

We claim:

1. An isolated obligately anaerobic lactic acid bacterium that has been mutated from being facultatively anaerobic to being obligately anaerobic so that the bacterium does not grow or has a very low growth rate in an aerobic environment but is capable of growing in an anaerobic environment, wherein the bacterium is *Lactobacillus acidophilus, Lactobacillus gasseri, Lactobacillus johnsonii, Lactobacillus helveticus, Lactobacillus salivarius, Lactobacillus delbrueckii, Lactobacillus plantarum, Lactobacillus casei, Lactobacillus rhamnosus, Lactobacillus rueteri*, or *Lactobacillus paracasei*.

2. The obligately anaerobic lactic acid bacterium according to claim 1, wherein the bacterium is capable of being transformed by an expression vector.

3. The obligately anaerobic lactic acid bacterium according to claim 2, wherein the expression vector is an expression vector into which has been introduced a gene expressing a protein having activity useful for the treatment of a disease that is in an anaerobic environment.

4. The obligately anaerobic lactic acid bacterium according to claim 1, wherein the *Lactobacillus* is *Lactobacillus casei*.

5. A pharmaceutical composition comprising as an active ingredient the obligately anaerobic lactic acid bacterium according to claim 1.

6. An antitumor drug comprising the pharmaceutical composition according to claim 5 and an antitumor substance precursor that is converted into an antitumor substance by a protein having activity in converting an antitumor substance precursor into an antitumor substance.

7. An isolated obligately anaerobic lactic acid bacterium that has been mutated from being facultatively anaerobic to being obligately anaerobic so that the bacterium does not grow or has a very low growth rate in an aerobic environment but is capable of growing in an anaerobic environment, wherein the bacterium is *Lactobacillus casei* KK378 (NPMD Accession No.: NITE BP-654) or a transformed bacterium thereof.

8. The obligately anaerobic lactic acid bacterium according to claim 7, wherein the transformed bacterium of *Lactobacillus casei* KK378 is *Lactobacillus casei* KJ686 (NPMD Accession No.: NITE BP-615).

9. The obligately anaerobic lactic acid bacterium according to claim 7, wherein the transformed bacterium of *Lactobacillus casei* KK378 is *Lactobacillus casei* KJ474 (NPMD Accession No.: NITE BP-1303).

10. An isolated obligately anaerobic lactic acid bacterium that has been mutated from being facultatively anaerobic to being obligately anaerobic so that the bacterium does not grow or has a very low growth rate in an aerobic environment but is capable of growing in an anaerobic environment, wherein the bacterium is transformed with an expression vector that functions in an obligately anaerobic lactic acid bacterium, the vector comprising a *Lactobacillus* plasmid replication protein gene (Rep), a secretion signal sequence (PslpA-SSartP) comprising a *Lactobacillus* s-layer gene promoter and a *Lactobacillus* PrtP protein secretion signal, and one or more selection marker genes.

11. A pharmaceutical composition comprising as an active ingredient the obligately anaerobic lactic acid bacterium according to claim 10.

12. An antitumor drug comprising a combination of the pharmaceutical composition according to claim 11 and an antitumor substance precursor that is converted into an antitumor substance by a protein having activity in converting an antitumor substance precursor into an antitumor substance.

* * * * *